United States Patent
Lebaron

(10) Patent No.: US 10,819,040 B1
(45) Date of Patent: Oct. 27, 2020

(54) ANTENNA HAVING DIPOLE PAIRS

(71) Applicant: Micron Medical LLC, Boca Raton, FL (US)

(72) Inventor: Richard Lebaron, Surprise, AZ (US)

(73) Assignee: Micron Medical LLC, Boca Raton, FL (US)

( * ) Notice: Subject to any disclaimer, the term of this patent is extended or adjusted under 35 U.S.C. 154(b) by 0 days.

(21) Appl. No.: 16/828,256

(22) Filed: Mar. 24, 2020

(51) Int. Cl.
| | |
|---|---|
| *H01Q 21/06* | (2006.01) |
| *H01Q 21/26* | (2006.01) |
| *A61N 1/378* | (2006.01) |
| *A61N 1/372* | (2006.01) |
| *H01Q 21/00* | (2006.01) |

(52) U.S. Cl.
CPC ......... *H01Q 21/062* (2013.01); *A61N 1/3787* (2013.01); *A61N 1/37229* (2013.01); *H01Q 21/0025* (2013.01)

(58) Field of Classification Search
CPC .. H01Q 21/062; H01Q 21/0025; H01Q 21/26; A61N 1/3787; A61N 1/37229
See application file for complete search history.

(56) References Cited

U.S. PATENT DOCUMENTS

| | | | |
|---|---|---|---|
| 6,028,565 | A | 2/2000 | Mackenzie et al. |
| 6,342,866 | B1 * | 1/2002 | Ho .................. H01Q 1/38 343/795 |
| 6,377,216 | B1 | 4/2002 | Cheadle et al. |
| 10,541,468 | B2 | 1/2020 | LeBaron et al. |
| 2002/0123289 | A1 | 9/2002 | DeAngelis et al. |
| 2005/0235482 | A1 | 10/2005 | Deaett et al. |
| 2006/0214867 | A1 * | 9/2006 | Chen .................. H01Q 9/285 343/795 |
| 2007/0210973 | A1 | 9/2007 | Tanaka et al. |
| 2008/0160851 | A1 | 7/2008 | Dunn et al. |
| 2009/0295657 | A1 | 12/2009 | Gakhar et al. |
| 2011/0012788 | A1 | 1/2011 | Rowell et al. |
| 2013/0056689 | A1 | 3/2013 | Zhang et al. |
| 2014/0180365 | A1 | 6/2014 | Perryman et al. |
| 2014/0318699 | A1 | 10/2014 | Longinotti-Buitoni et al. |
| 2016/0149293 | A1 | 5/2016 | Walker |
| 2016/0184597 | A1 | 6/2016 | Andresen et al. |

* cited by examiner

*Primary Examiner* — Hoang V Nguyen
(74) *Attorney, Agent, or Firm* — Banner & Witcoff, Ltd.

(57) ABSTRACT

An antenna having dipole pairs is described. The antenna may include a plurality of dipole elements, intermediate conductors, each being electrically connected to one of the plurality of dipole elements, and feed conductors capacitively coupled to the intermediate conductors. The antenna may further include tuning loops.

27 Claims, 22 Drawing Sheets

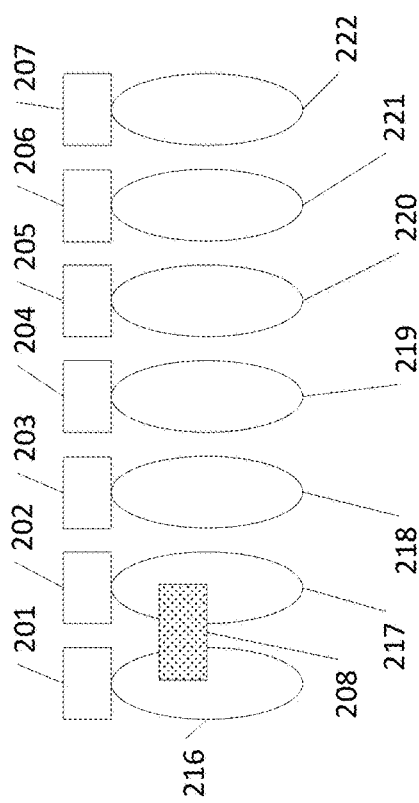
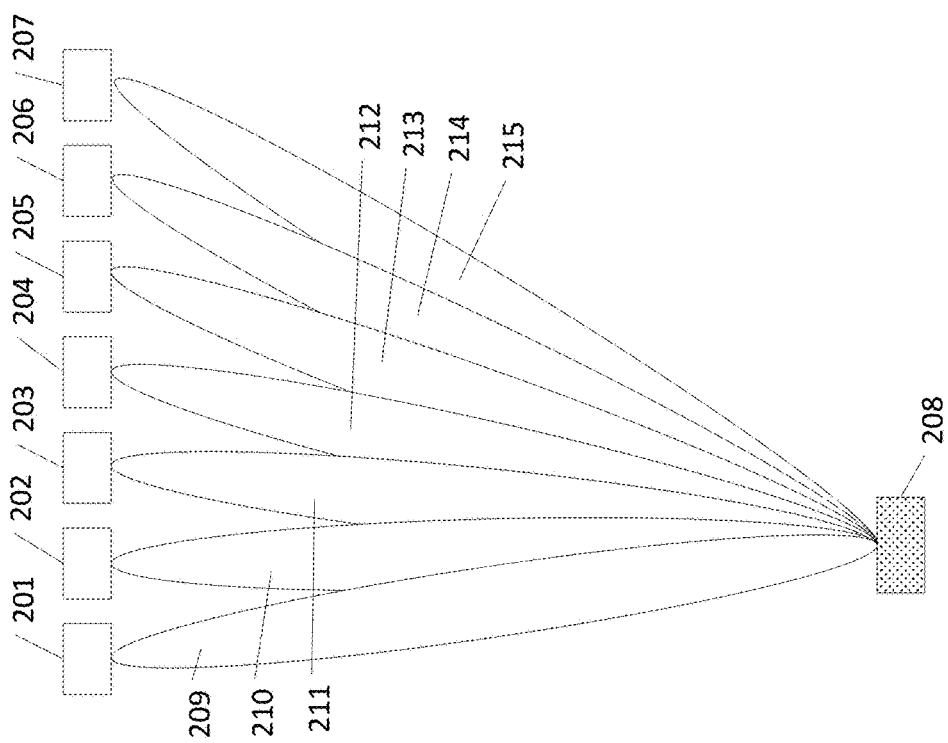
Figure 2B
Figure 2A

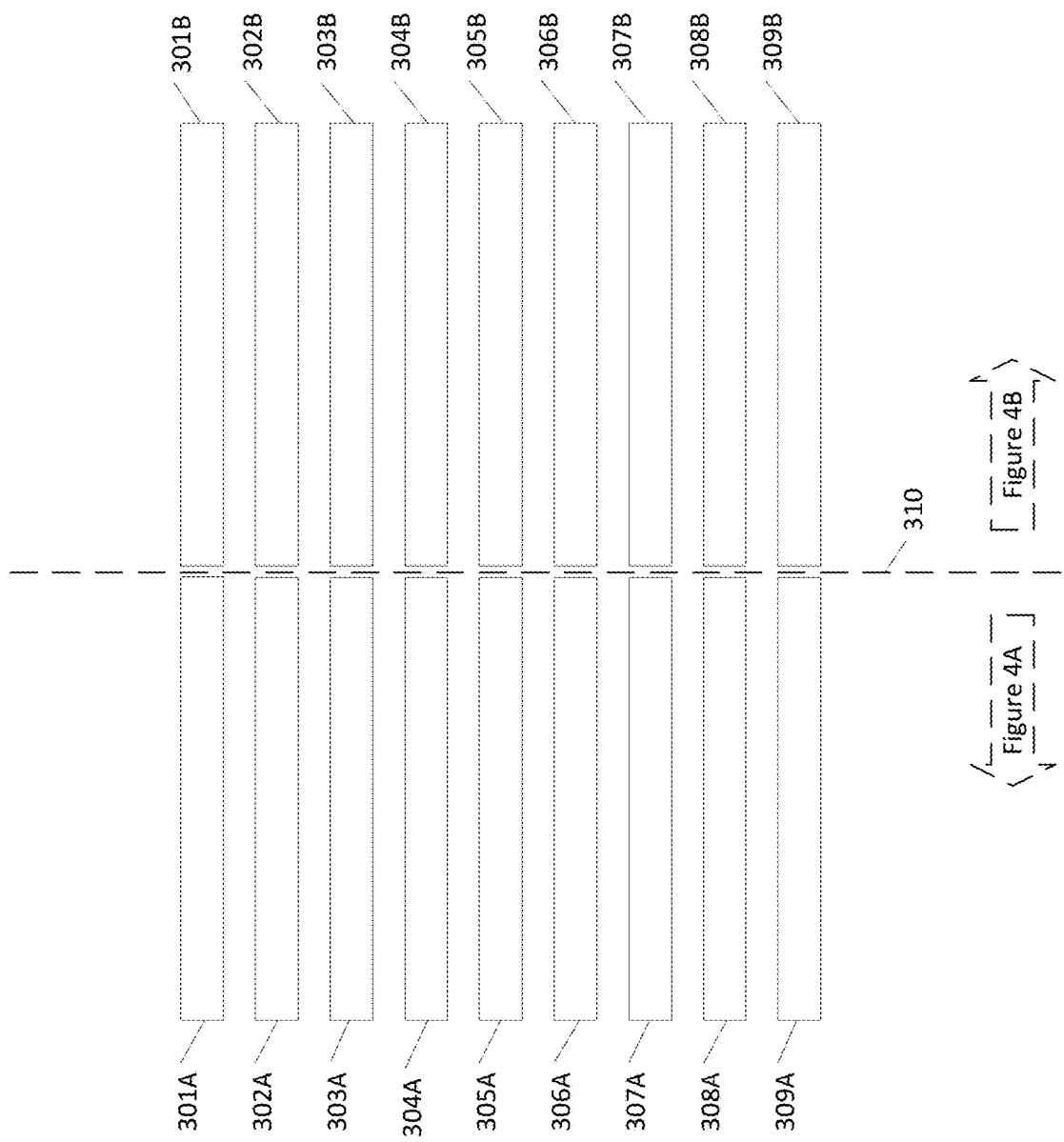

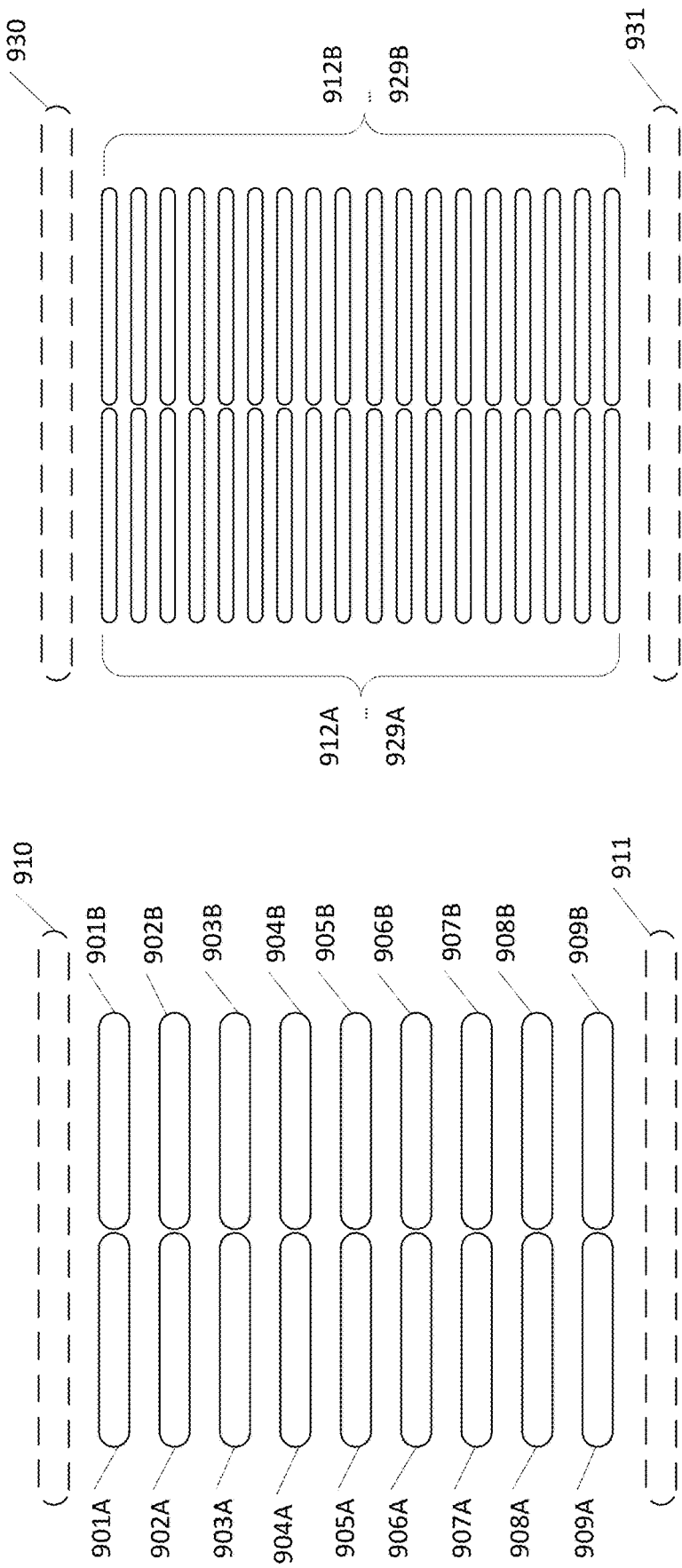

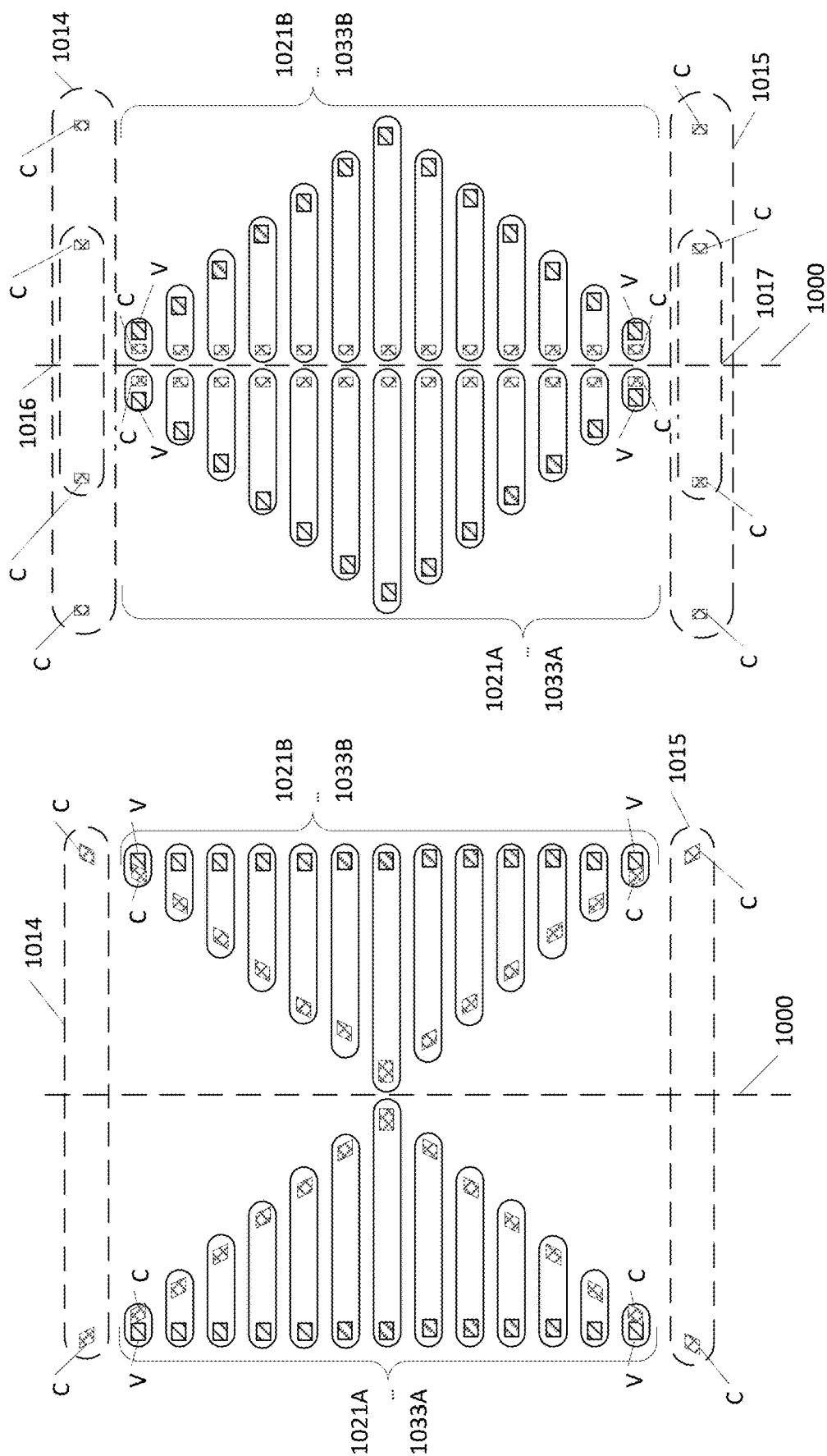

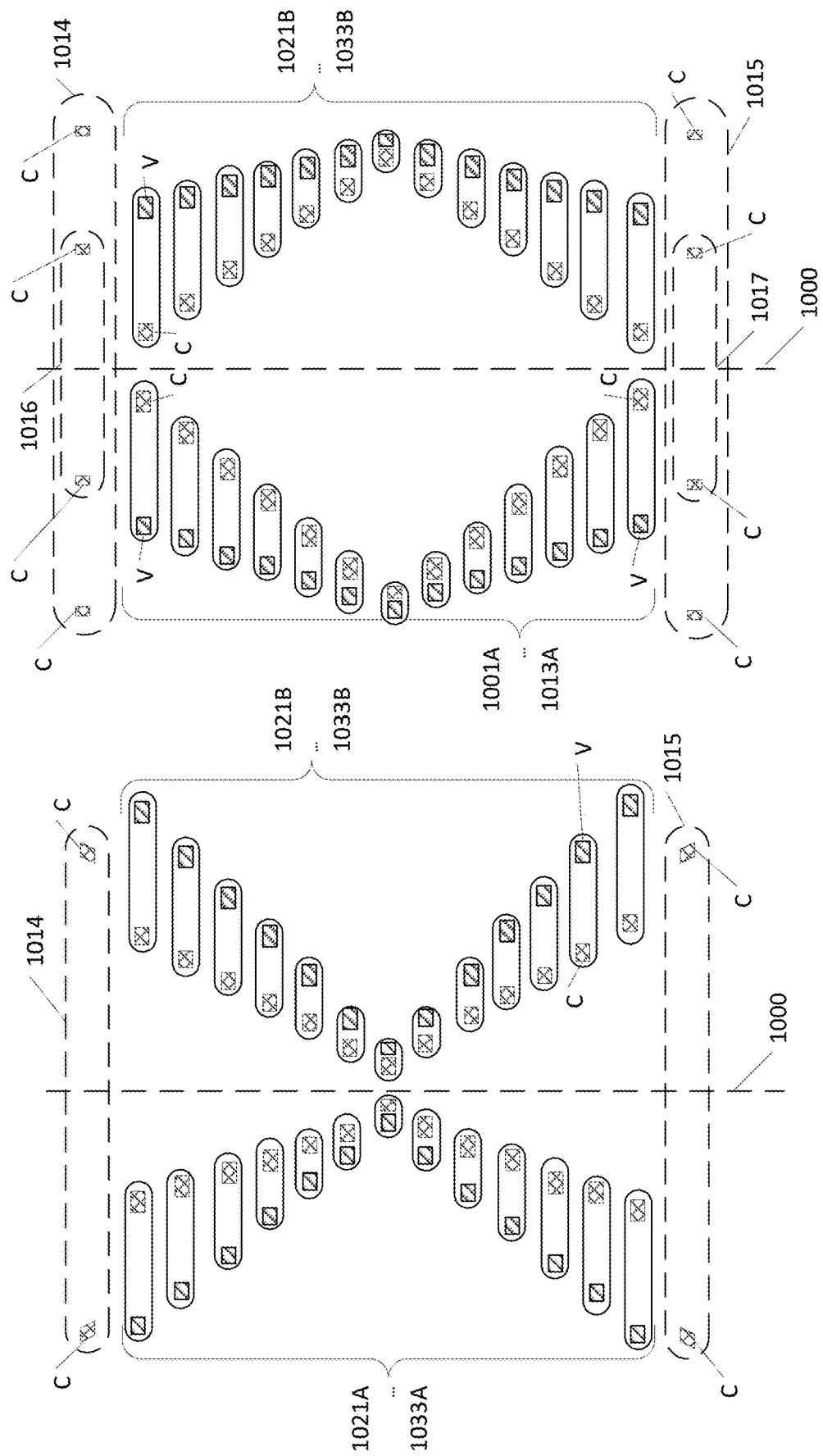

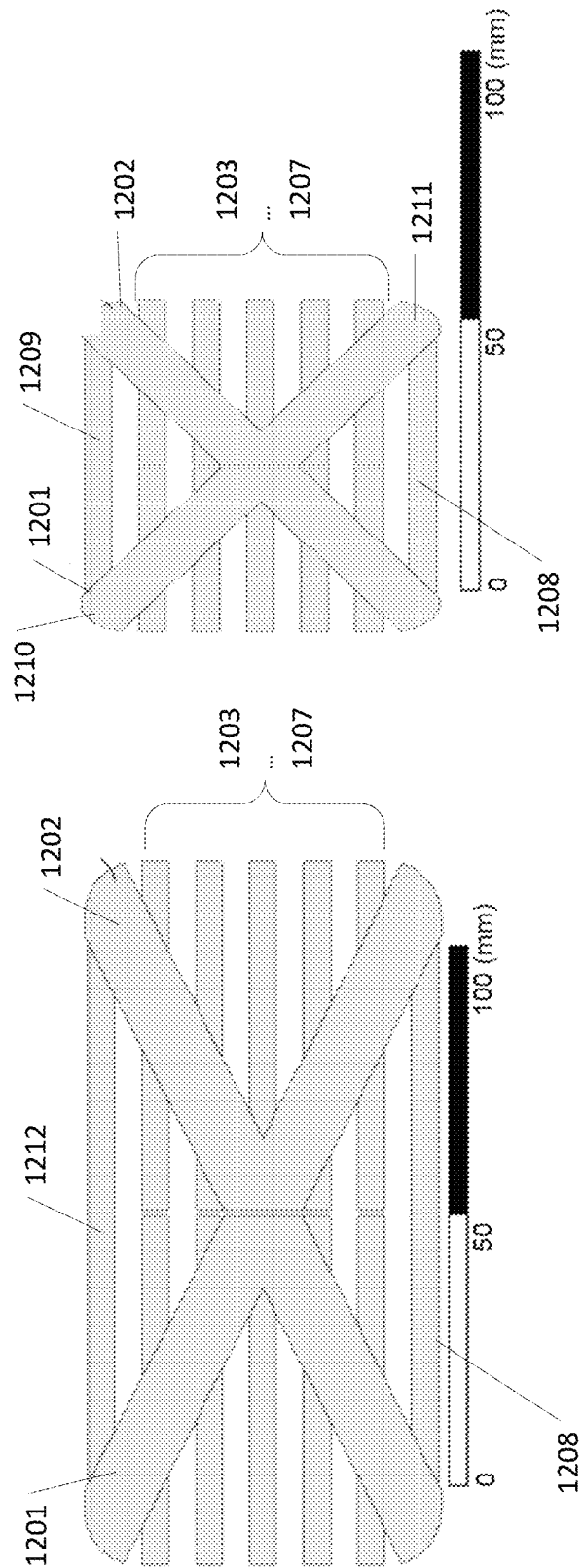

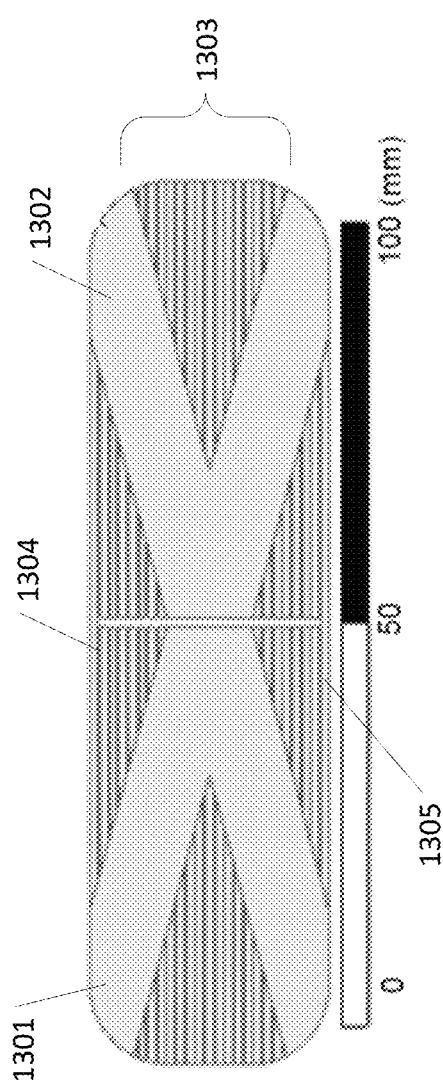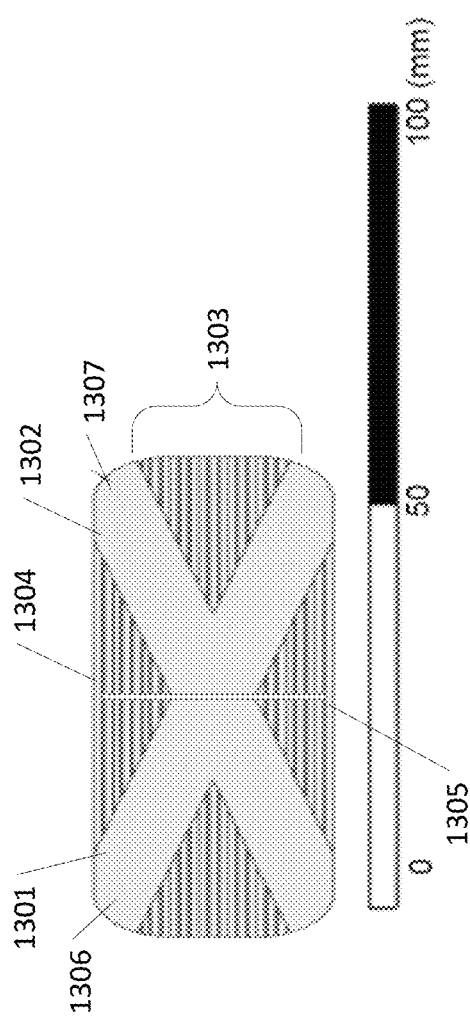

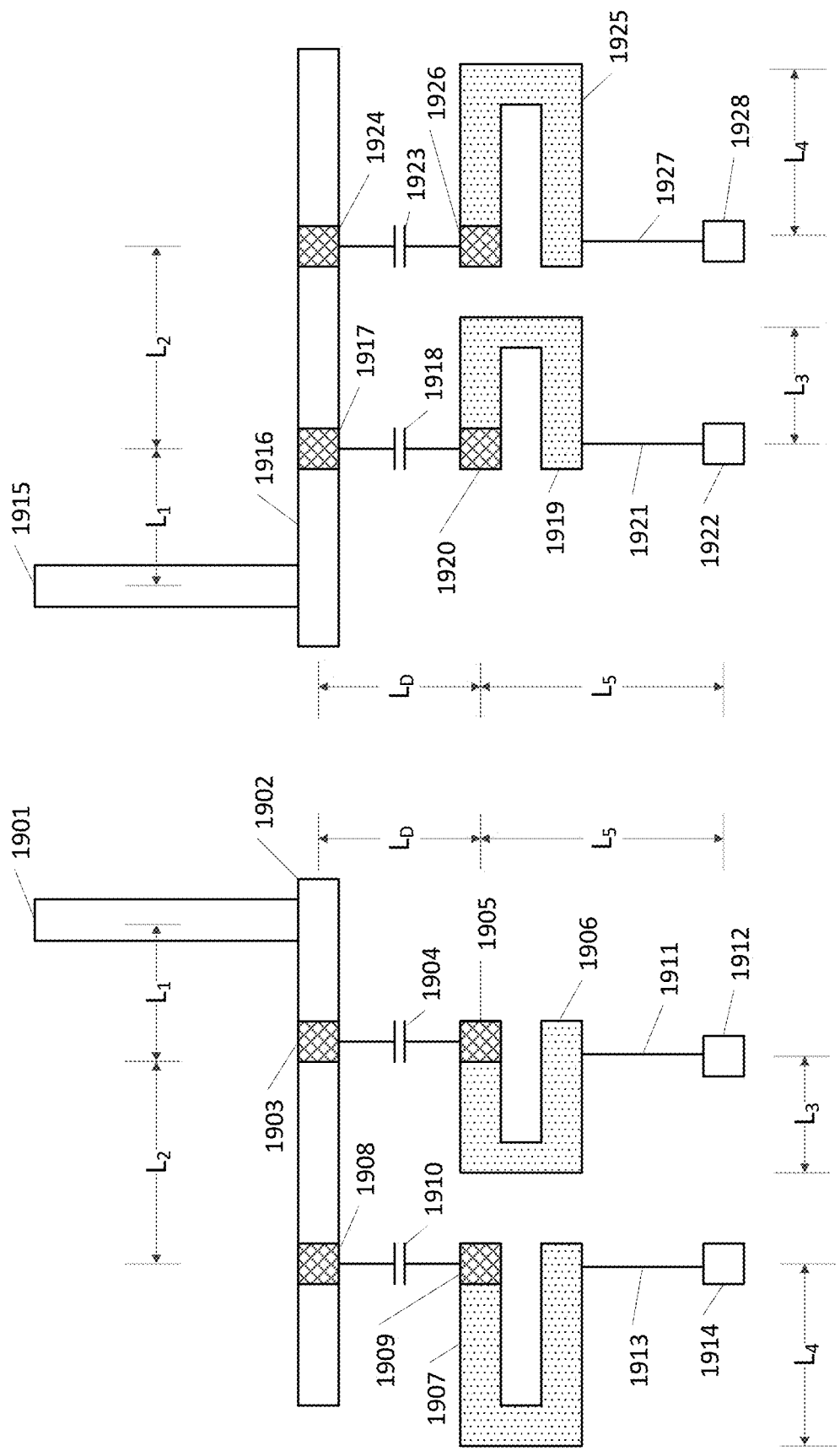

ANTENNA HAVING DIPOLE PAIRS

TECHNICAL FIELD

This disclosure relates to an antenna having dipole pairs.

BACKGROUND

Modulation of tissue within the body by electrical stimulation has become an important type of therapy for treating chronic, disabling conditions, such as chronic pain, problems of movement initiation and control, involuntary movements, dystonia, urinary and fecal incontinence, sexual difficulties, vascular insufficiency, and heart arrhythmia. For example, an external antenna may be used to send electrical energy to electrodes on an implanted tissue stimulator that can pass, to the tissue, pulsatile electrical signals including one or more of controllable frequency, controllable pulse width, and/or controllable amplitudes. Antennas have been designed and used with implanted devices to aid in the treatment of various medical conditions. Often, these antennas are placed close to the patient's body. In some cases, the conductive element of the antennas would be subject to excessive absorption of electromagnetic energy, which, when these antennas are placed close to the patient's body, could lead to adverse events such as burning of tissue, creation of undesirable blood clots and skin irritation from adherence of the antenna directly to skin tissue. Also, in some cases, an antenna may be uncomfortable due to its overall size. However, due to design constraints, antennas resist minimization.

SUMMARY

In general, this disclosure relates to an antenna having dipole pairs. The antenna may be used to transmit at least one of power and/or digitized data information with an implanted device with an integrated or coupled receiver, whereas the antenna has a smaller footprint while providing equivalent characteristics to those of larger antennas.

In one aspect, an antenna may include two or more dipole elements and a feed conductor separated from the two or more dipole elements by a first dielectric. In another aspect, the antenna may further include the dipole elements, the first dielectric, an intermediate conductor, and the feed conductor. In yet another aspect, the quantity and size of each pair of dipole elements may be the same or different. In a further aspect, the antenna may comprise one or more loop segments.

Additional aspects, configurations, embodiments, and examples are described in more detail below.

DESCRIPTION OF DRAWINGS

Certain manufacturing techniques and manufactured devices are described below with reference to the accompanying figures.

FIG. 2A shows an example of an antenna creating a far field radiation pattern. FIG. 2B shows an example of an antenna creating a near field radiation pattern.

FIG. 3 shows an array of dipole elements.

FIG. 9A shows a dipole array with nine dipole pairs. FIG. 9B shows a dipole array with 18 dipole pairs.

FIG. 10C shows a first example of intermediate conductors of different lengths. FIG. 10D shows a second example of intermediate conductors of different lengths. FIG. 10G shows a fifth example of intermediate conductors of different lengths. FIG. 10H shows a sixth example of intermediate conductors of different lengths.

FIG. 12A shows another antenna with a feed conductor layer. FIG. 12B shows another antenna with a feed conductor layer having at least one smaller dimension than that of the antenna of FIG. 12A.

FIG. 13A shows yet another antenna with a feed conductor layer. FIG. 13B shows yet another antenna with a feed conductor layer having at least one smaller dimension than that of the antenna of FIG. 13A.

FIG. 19A shows an elevation view of two dipole elements connected to respective conductive layers where the conductive layers have different lengths. FIG. 19B shows an elevation view of two dipole elements connected to respective conductive layers where the conductive layers have different lengths, where the two dipole elements are complementary to those of FIG. 19A.

Figure 1:
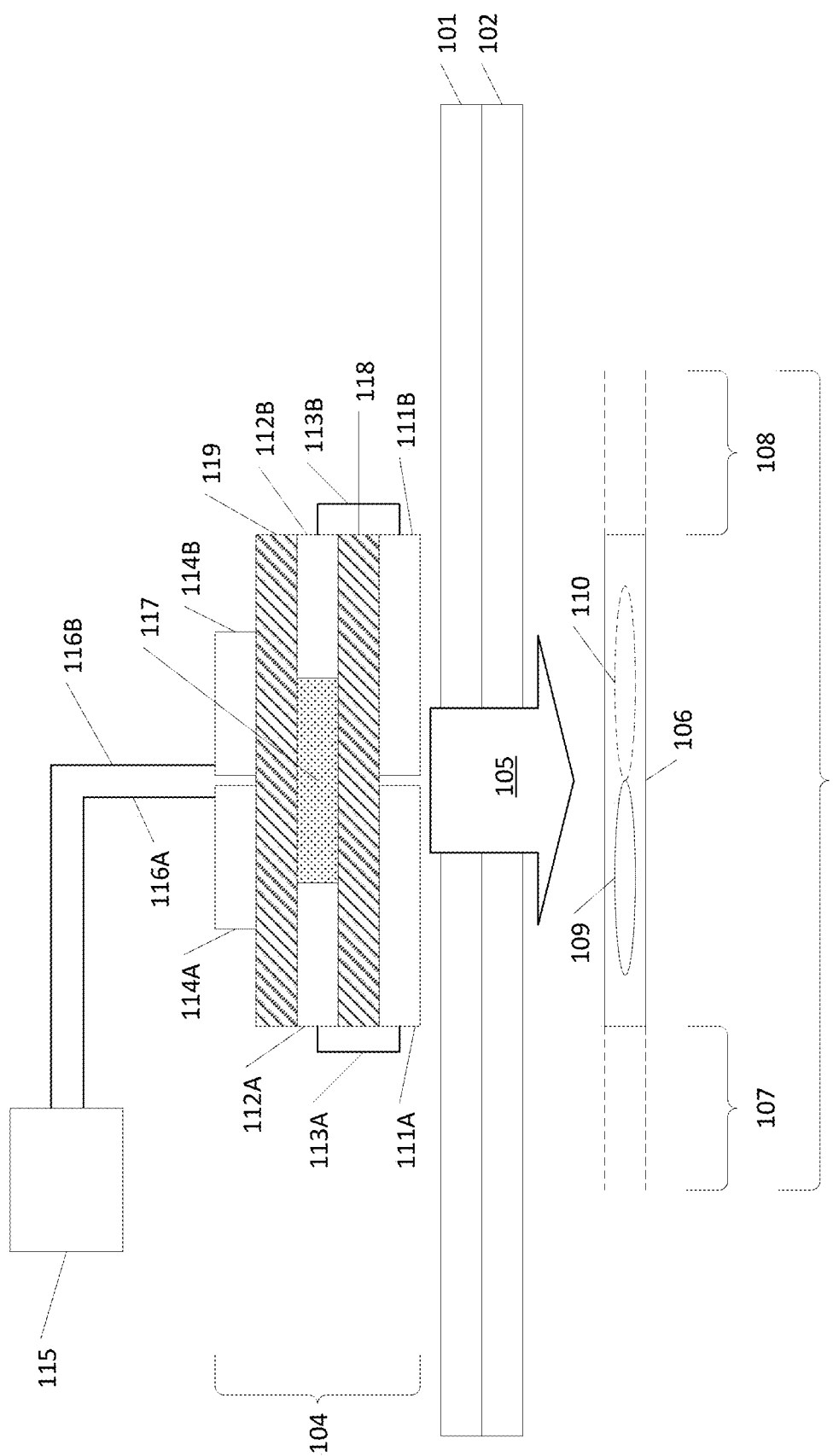
FIG. 1 shows an example of an elevation view of an antenna sending a wireless signal to an implanted device with an integrated or coupled receiver.

Other aspects of the disclosure may be found throughout the application. The size bars in various figures are provided for a comparison of relative scales.

DETAILED DESCRIPTION

Certain improvements to an antenna are described. The various arrangements may include one or more of multiple conducting layers that increase a path length to dipole pairs, permitting formation of an antenna with reduced dimensions. Some of the various arrangements may also include loops that aid in matching the impedance of the antenna to RF circuitry while also aiding in the focusing of the radiation emitted via the antenna.

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power a passive implanted wireless stimulator device. The targeted nerves may include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

Recent years have seen a surge of demand for wearable antennas that are flexible in shape to tailor to that of human body and robust to withstand daily wear and tear. Indeed, wearable antennas may be used for radiating from the body surface into air, and receiving a signal from air on the body surface. While some examples may use wearable antennas primarily for RF communications, some implementations disclosed herein employ wearable antenna to radiate RF energy into the body to wireless power and communicate with a passive stimulator device implanted in the patient.

Patient ergonomics and comfort mandate the wearable antennas to be thin, light weight, flexible, and conformal to the body. These traits need to be reconciled with performance characteristics for the substrate materials to be lossless and electrically stable when introduced to the body. Specifically, the materials need to be breathable but must not absorb or retain moisture, which may cause changes in an antenna's electrical properties, and therefore the antenna's performance.

There are at least two advantages to using an antennas comprising an array of radiating elements compared to using a single antenna with a single radiating element. One such advantage is the ability to distribute power as it enters the body, thereby reducing SAR hot spots at the patient's skin. The other advantage is the ability to focus the transmitted energy in the body, for more efficient energy transmission. If the phase is incorrect, constructive interference may not occur at the intended area to realize the gains that would have resulted from the use of multiple transmitting sources. The electric field from all of the radiating elements may be superposed at the same spot at the same time (focused) such that maximum field intensity may be attained and energy is not wasted.

A wireless stimulation system may include an implantable stimulator device with one or more electrodes and one or more conductive antennas (for example, dipole or patch antennas), and internal circuitry for frequency waveform and electrical energy rectification. The system may further comprise an external controller and antenna for transmitting radio frequency or microwave energy from an external source to the implantable stimulator device with neither cables nor inductive coupling to provide power.

For purposes of explanation, the following terms are used in this disclosure. "Antenna" generally refers to a radiation-emitting structure. That structure may comprise a pair of radiation-emitting elements or may comprise one or more arrays of radiation elements. A "dipole pair" generally refers to two dipole elements separated by a gap. A "dipole element" generally refers to one of the elements of a dipole pair. A "dipole array" generally refers to a combination of two or more dipole pairs.

Various examples of the antenna having dipole pairs may have different levels of rigidity. For example, with respect to rigid structures, those structures may be inflexible based on the size and shape of the internal components of the antenna (e.g., one or more structures comprising a printed circuit board, an inflexible dielectric, or other rigid material). With respect to flexible structures, the structures may be flexible based on how components are connected to each other (e.g., two inflexible printed circuit boards connected by a flexible hinge or other flexible connector) or the underlying material used for the components. For example, the conductors described herein (dipole elements, electrical conductors, feed conductors, and the like) may be printed using electrically conductive ink on a flexible substrate (e.g., a dielectric of a flexible material, a fabric such as LYCRA™-brand fabric (LYCRA is a trademark of the LYCRA Company of Wilmington, Del.), cotton, nylon, and/or other materials usable as fabrics. The antenna as described herein may be rigid across its dimensions, rigid across at least one dimension while being flexible across another dimension, and/or flexible across all dimensions.

In various implementations, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil.

According to some implementations, a wireless stimulation system may include an antenna assembly coupled to a controller module and configured to radiate electromagnetic energy to an implantable device. In some instances, the implantable device may be a passive neural stimulator device configured to receive RF energy and stimulation parameters wirelessly. By using the received electromagnetic energy, the implantable passive neural stimulator creates one or more stimulation pulses to stimulate neural tissue of a patient. In particular, the antenna assembly may include an antenna with feed connectors connected to feed ports. The feed ports, one per feed connector (a coax connector, e.g., a BNC connector or an SMA connector), may be coupled to a controller module that drives the antenna to transmit the electromagnetic energy from the antenna. The antenna may be generally sized and shaped to radiate the electromagnetic energy to match a reception characteristic of the implantable passive neural stimulator. In one example, the implantable passive neural stimulator includes an antenna configured to receive polarized electromagnetic energy commensurate with dipole reception characteristics.

The wearable antenna may include an antenna in which pairs of conductive dipole elements form dipole pairs, where each dipole element is separated from its pair by a gap. The dipole pairs may be arranged in parallel. The conductive material forming the dipole elements may include conductive ink printed on fabric material or as part of a printed circuit board or other substrate. A feed layer may be provided above the dipole pairs, the feed layer having two halves, each being connected to a phase of an RF source. The feed layer may include an X-shaped conductor trace (having a central gap that divides the feed layer into symmetric halves), an I-shaped conductor trace (also having a central gap), or other shape or shapes. The feed points (one or more per half) may be located on each half and located at a central portion of each feed layer. In one example, each feed point may be connected to one conductor of a coaxial cable, one or more conductors of wires, and the like.

The antenna may further comprise intermediate conductors electrically connected to the dipole elements and capacitively coupled to the feed conductors. While not radiating a signal like the dipole pairs, the intermediate conductors may increase a path length to the dipole elements, thereby permitting the adjustment of the phase of a signal from a given dipole pair to create a radiation pattern at the gaps that is effectively in phase (e.g., within 0-15%) with at least the phase of the radiation from the surrounding dipole pairs. The array of dipole pairs may be configured to be operable to form a constructive interference over a region where the passive implantable stimulator device has been implanted. Further, tuning loops may be positioned at the ends of the dipole array to create destructive interference with the radiated signal. Further, the tuning loops may permit tuning of the impedance by adding an inductive component to the antenna's capacitive nature.

The radiating surface of the transmitting antenna may be generally sized and shaped to radiate the electromagnetic energy to match a reception characteristic of the implantable passive neural stimulator. In one example, the implantable passive neural stimulator includes an antenna and the radiating surface is configured to transmit a linearly polarized electric field commensurate with dipole reception characteristics.

An RF pulse generator module may include communication electronics that support the wireless connection, the stimulation circuitry, and the battery to power the generator electronics. In some implementations, the RF pulse generator module includes the transmit antenna embedded into its packaging form factor while, in other implementations, the transmit antenna is connected to the RF pulse generator module through a wired connection. The transmit antenna may be coupled directly to tissue to create an electric field that powers the implanted wireless stimulator device. The transmit antenna may communicate with the implanted wireless stimulator device through an RF interface. For instance, the transmit antenna radiates an RF transmission signal that is modulated and encoded by the RF pulse generator module. The implanted wireless stimulator device of module contains one or more antennas, such as antenna (s), to receive and transmit through RF interface. In particular, the coupling mechanism between a transmitting antenna and the one or more antennas on the implanted wireless stimulation device of module may use an electrical radiative coupling, or electrical near-field coupling and not an inductive coupling. In other words, the coupling may occur through electric fields rather than magnetic fields.

Through this electrical radiative coupling, the transmit antenna may provide an input signal to the implanted wireless stimulator device. This input signal contains energy and may optionally contain information encoding additional control parameters, e.g., identification of waveforms to be applied at the electrodes of the implanted wireless stimulator device. The optional information may include identification of an amplitude, a pulse length, a wave pattern, or related information. In some implementations, the power level of the input signal may directly determine an applied amplitude (for example, power, current, or voltage) of the one or more electrical pulses created using the received electrical energy. In other implementations, the applied amplitude may be independent of the input power. The implanted wireless stimulator device may contain components for demodulating the RF transmission signal and electrodes to deliver the stimulation to surrounding neuronal tissue.

The RF pulse generator module may be implanted subcutaneously, or it may be worn external to the body. When external to the body, the RF generator module may be incorporated into a belt or harness design to allow for electric radiative coupling through the skin and underlying tissue to transfer power and/or control parameters to the implanted wireless stimulator device. In either example, one or more receiver circuits internal to the wireless stimulator device may capture the energy radiated by the transmit antenna and convert this energy to an electrical waveform. The receiver circuit(s) may further modify the waveform to create an electrical pulse suitable for the stimulation of neural tissue.

The RF pulse generator module may be connected via wired connection to an external transmitting antenna. Alternatively, both the antenna and the RF pulse generator may be located subcutaneously beneath the skin. The signals sent by RF pulse generator module to the implanted wireless stimulator device may include both power and parameter-setting attributes in regards to stimulus waveform, amplitude, pulse width, and frequency. The RF pulse generator module may also function as a wireless receiving unit that receives feedback signals from the implanted wireless stimulator device. The RF pulse generator module may contain microelectronics or other circuitry to handle the generation of the signals transmitted to the device as well as handle feedback signals, such as those from the stimulator device. For example, the RF pulse generator module may comprise controller subsystem, high-frequency oscillator, RF amplifier, a RF switch, and a feedback subsystem or other components as desired.

In some applications, the transmit antenna may be placed in close proximity to the receiving antenna. For example, the transmit antenna may be worn by the patient. In other examples, the transmit antenna may be placed further away from the patient (and the implanted passive neural stimulator that houses receiving antenna). In the former case, less energy may be emitted from the remote antenna to wirelessly provide power and stimulation parameter settings to the stimulator. In some scenarios, the patient may remain stationary or asleep. During sleep, the patient may not desire to wear a transmitting antenna that is coupled to a controller module (such as controller subsystem) through a cable. An antenna assembly may be used to remotely provide power and stimulation parameter settings to the stimulator. The antenna assembly in this example may be more than centimeters away from the passive neural stimulator implanted inside a patient. If the patient may move around a room; the entire room may need to be illuminated with the microwave energy field. In this scenario, a plurality of antennas, or a broad beam-width antenna, may be used. Some implementations may incorporate a steerable (e.g., mechanically, electrically) arrangement of antennas that include a receiving antenna location tracking system. These implementations may further apply motion control of the transmitting antenna to adjust angle or orientation of illumination of an antenna to point in the direction of the receiving antenna.

The output power is adjusted as needed depending on the distance between the transmitting and receiving antennas and the directivity of the transmitting antenna.

An antenna design may be modified to achieve a more selective spatial transmission profile so that radiated energy may be more concentrated, or distributed as needed, at the location of the implantable stimulator device.

The process of manufacturing the antenna may include printing the silver ink trace onto a transfer sheet, via screen printing; and then adding a thin dielectric layer, via screen printing, to prevent any oxidation of the silver ink trace. While this printing step may suffice for a single layer fabric antenna, for multiple layer arrays, a second layer of silver conductive ink maybe printed on top of the dielectric layer, the dielectric layer isolating the two conducive layers.

The silver conductive ink trace and dielectric insulator stack with the transfer sheet may then be applied to an elastic fabric, such as, for example, elastic polyurethane material including LYCRA™. The application may involve a hot press process using, for example, a hot press machine, or any clothing iron. This process step may be very similar to that of applying a typical iron-on patch to clothing. The RF feed cable may then be attached to the silver ink conductive layer by applying a conductive epoxy to end of the cable and to the antenna at its feed point. Thereafter, a thin adhesive layer may be used to add a top layer of elastic fabric, resulting in a flexible, breathable, conformable fabric antenna that may be embedded in clothing. In this manner, a fabric antenna configuration may be implemented to allow a human patient who has received an implantable stimulator device to engage in daily routines while wearing the antenna assembly. The fabric antenna serves as a non-inductive interface to transmit electric energy wirelessly into the passive implantable stimulator device that does not have a battery. In some cases, the fabric antenna may also wirelessly receive signals, such as telemetry signals, from the implantable stimulator device. The fabric antenna may be part of a microwave field stimulator (MFS) device that is external to the human patient. In some cases, the fabric antenna may be connected to the controller portion of the MFS device.

FIG. 1 shows an example of an elevation view of an antenna sending a wireless signal to an implanted device (e.g., an implanted nerve stimulator 103). FIG. 1 shows a patient's skin layer 101 and a subcutaneous layer of fat 102. Below the layer of fat 102, a stimulator 103 is implanted. The stimulator 103 receives a radio frequency signal 105 from an external antenna 104, via the stimulator's antenna 106. The stimulator 103 may also include a section 107 with exposed electrodes that apply an electrical signal to surrounding tissues. The stimulator 103 may include an additional section with electrical components that drive the exposed electrodes. The electrical components may be located between antenna 106 and the exposed electrodes of section 107 or may be located in another section, for example, in section 108. The antenna 106 may include one or more antenna elements 109 with optional element 110.

Signal 105 may be transmitted to antenna 106 via an external antenna 104. The external antenna 104 may comprise one or more dipole pairs 111A, 111B.

The dipole element 111A is electrically coupled to an intermediate conductor 112A by an electrical conductor 113A. The dipole element 111B is electrically coupled to an intermediate conductor 112B by an electrical conductor 113B. Electrical conductors 113A, 113B may comprise the same material as dipole elements 111A, 111B, may comprise the same material as intermediate conductors 112A, 112B, or may comprise another material (e.g., an electrically conductive via connecting wiring traces).

The intermediate conductor 112A is capacitively coupled to a feed conductor 114A. The intermediate conductor 112B is capacitively coupled to a feed conductor 114 B. The feed conductors 114A, 114B receive radiofrequency signals from a radiofrequency source 115, via electrical conductors 116A and 116B, respectively.

Dipole elements 111A, 111B may be separated from the intermediate conductors 112A, 112B by dielectric 118. Dipole elements 111A, 111B may be separated from each other by an air gap, dielectric 118, or another dielectric. Intermediate conductors 112A, 112B may be separated from the feed conductors 114A, 114B by the dielectric 119. The intermediate conductors 112A, 112B may be separated by a dielectric 117. The dielectric 117 may comprise the same or similar material as that of one or more of dielectric 118 or dielectric 119 or another material.

FIG. 2A shows an example of an antenna creating a far field radiation pattern. FIG. 2A comprises a quantity of dipole elements 201-207 and an implanted nerve stimulator 208. The quantity of dipole elements 201-207 form, by known beam forming techniques, beams 209-215. For reference, the dipole elements 201-207 in FIG. 2A are operating in a far field operation mode (e.g., adjacent dipole pairs receiving a signal in a slightly different phase).

FIG. 2B shows an example of an antenna creating a near field radiation pattern. FIG. 2B comprises the dipole elements 201-207 and the implanted nerve stimulator 208. The quantity of dipole elements 201-207 form, by known beam forming techniques, beams 216-222. For reference, the dipole elements 201-207 in FIG. 2B are operating in a near field operation mode (e.g., adjacent dipole pairs receiving a signal in the same phase).

FIG. 3 shows an array of dipole elements. The array comprises nine dipole pairs. The quantity of dipole pairs may be increased or decreased as desired. FIG. 3 shows dipole elements 301A-309A on left side of centerline 310 ad dipole elements 301B-309B on the right side of centerline 310. In a near field operation of the array of FIG. 3, the beams formed by the dipole pairs may, at the centerline 310, generate beams having the same phase. To adjust the phases of the beams at each dipole pair to be the same at centerline 310, various adjustments may be made to one or more of the following: the path length of a feed conductor to each dipole pair, the dimensions of each dipole, the location of where the feed conductor attaches to each dipole, the distance between the feed conductor and each dipole, the dielectric constant of the material separating the feed conductor and each dipole, the distances between adjacent dipole pairs (e.g., in the direction along centerline 310) and the like.

Figure 4B:
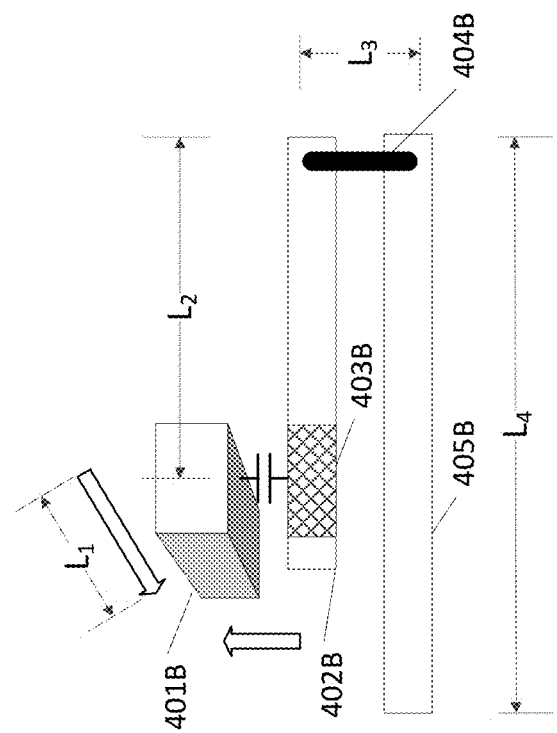
FIG. 4B shows a complementary second dipole element with another intermediate conductor and another feed conductor layer.
Figure 4A:
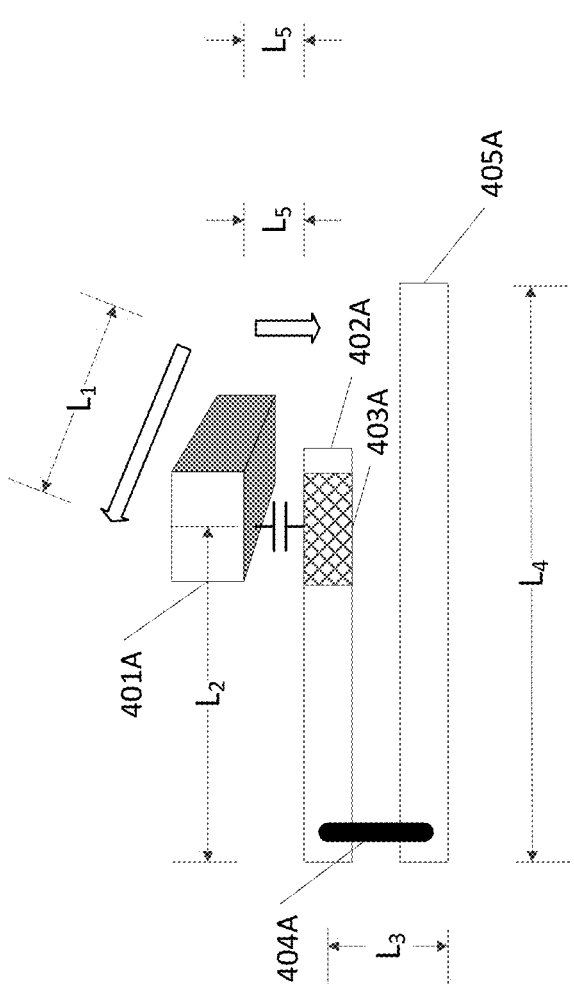
FIG. 4A shows a first dipole element, an intermediate conductor, and a feed conductor layer.

FIGS. 4A and 4B show complementary views looking outward from centerline 310 of FIG. 3, as represented by the directional arrows shown in dashed lines at the bottom of FIG. 3. FIG. 4A shows a feed conductor 401A and an intermediate conductor 402A. The feed conductor 401A is capacitively coupled to the intermediate conductor 402A. For the purpose of explanation, a first phase of a signal is represented by a down arrow near feed conductor 401A and intermediate conductor 402A. The coupling is represented in FIG. 4A by the capacitor between them. A portion 403A of the intermediate conductor 402A is shaded to identify the region that is coupled with the feed conductor 401A. The intermediate conductor 402A is electrically connected via an electrical conductor 404A to a dipole element 405A.

A path length of the feed conductor 401A, from a radio frequency (RF) feed location (not shown) to the location of the capacitive coupling with intermediate conductor 402A, is represented by length $L_1$. A path length along intermediate conductor 402A, from the capacitive coupling with the feed conductor 401A to the electrical conductor 404A, is represented as length $L_2$. A path length of electrical conductor 404A is represented as length $L_3$. A path length along dipole element 405A from electrical conductor 404A to a gap with a corresponding dipole element (e.g., a dipole element 405B of FIG. 4B) is represented as length $L_4$. A path length between feed conductor 401A and intermediate conductor 402A is represented as length $L_5$. Summing the various path lengths, an overall path length $L_A$ from the feed location of feed conductor 401A to the gap between the dipole element 405A and the dipole element 405B is represented by:

$$L_A = L_1 + L_2 + L_3 + L_4 + L_5 \quad (1)$$

FIG. 4B shows a feed conductor 401B and an intermediate conductor 402B. The feed conductor 401B is capacitively coupled to the intermediate conductor 402B. The coupling is represented in FIG. 4B by the capacitor between them. A portion 403B of the intermediate conductor 402B is shaded to identify the region that is coupled with the feed conductor 401B. The intermediate conductor 402B is electrically connected via an electrical conductor 404B to a dipole element 405B.

A path length of the feed conductor 401B, from a feed location (not shown) to the location of the capacitive coupling with intermediate conductor 402B, is represented by length $L_1$. A path length along intermediate conductor 402B, from the capacitive coupling with the feed conductor 401B to the electrical conductor 404B, is represented as length $L_2$. A path length of electrical conductor 404B is represented as length $L_3$. A path length along dipole element 405B from electrical conductor 404B to a gap with a corresponding dipole element (e.g., the dipole element 405A of FIG. 4A) is represented as length $L_4$. A path length between feed conductor 401B and intermediate conductor 402B is represented as length $L_5$. Summing the various path lengths, an overall path length $L_B$ from the feed location of feed conductor 401B to the gap between the dipole element 405A and the dipole element 405B is represented by:

$$L_B = L_1 + L_2 + L_3 + L_4 + L_5 \quad (2)$$

To minimize antenna inconsistences, the arrangements of FIGS. 4A and 4B may be symmetric about centerline 310, making the path lengths $L_A$ and $L_B$ equal to each other. For the purpose of explanation, a first phase of a signal is represented, in FIG. 4A, as a down arrow near feed conductor 401A and intermediate conductor 402A (e.g., representing a current flow for a given phase). That first phase is represented, in FIG. 4B, as an up arrow near feed conductor 401B and intermediate conductor 402B. In an opposite phase of the feed signal, the signal may be represented in FIG. 4A as an up arrow and in FIG. 4B as a down arrow.

The electrical conductors 404A, 404B are shown in FIGS. 4A and 4B as conductive vias, connecting conductive traces 402A, 402B, 405A, 405B (e.g., of a printed circuit board). The electrical conductors 404A, 404B may have other alternate or additional forms including a metal wire, a metalized structure (e.g., a resin, nylon, epoxy, or other material coated or/impregnated with a conductive material), a conductive trace on a printed circuit board connecting other conductive traces of the printed circuit board, an extended portion of a dipole element that is not collinear with the remainder of the dipole element. Further, intermediate conductors 402A, 402B may comprise material corresponding to that used to form dipole elements 405A, 405B, may comprise material corresponding to the electrical conductors 404A, 404B, may comprise material common to both, or comprise a material distinct from the dipole elements 405A, 405B and distinct from the electrical conductors 404A, 404B. As an example, the dipole elements 405A, 405B and the electrical conductors 404A, 404B may comprise copper wires that have been bent to connect to printed conductive alloy traces of a printed circuit board, where the printed conductive alloy traces correspond to the intermediate conductors 402A, 402B. In another example, the dipole elements 405A, 405B, the electrical conductors 404A, 404B, and the intermediate conductors 402A, 402B may be formed from conductive wires bent around a dielectric. For instance, a conductive wire or trace may comprise a first portion that operates as a dipole and a second portion at an angle relative to the first portion that, operating as an electrical conductor, connects to an intermediate conductor.

Further, the electrical conductor may be subsumed as part of an intermediate conductor. A dielectric separating a dipole from an intermediate conductor may be tapered at a distal end of a dipole element and the intermediate conductor connect directly to the distal end of the dipole element. As such the intermediate conductor maybe identified as a first portion (acting as an intermediate conductor) that is capacitively coupled to a feed conductor and a second portion that connects to a dipole element (acting as an electrical conductor).

Figure 5:
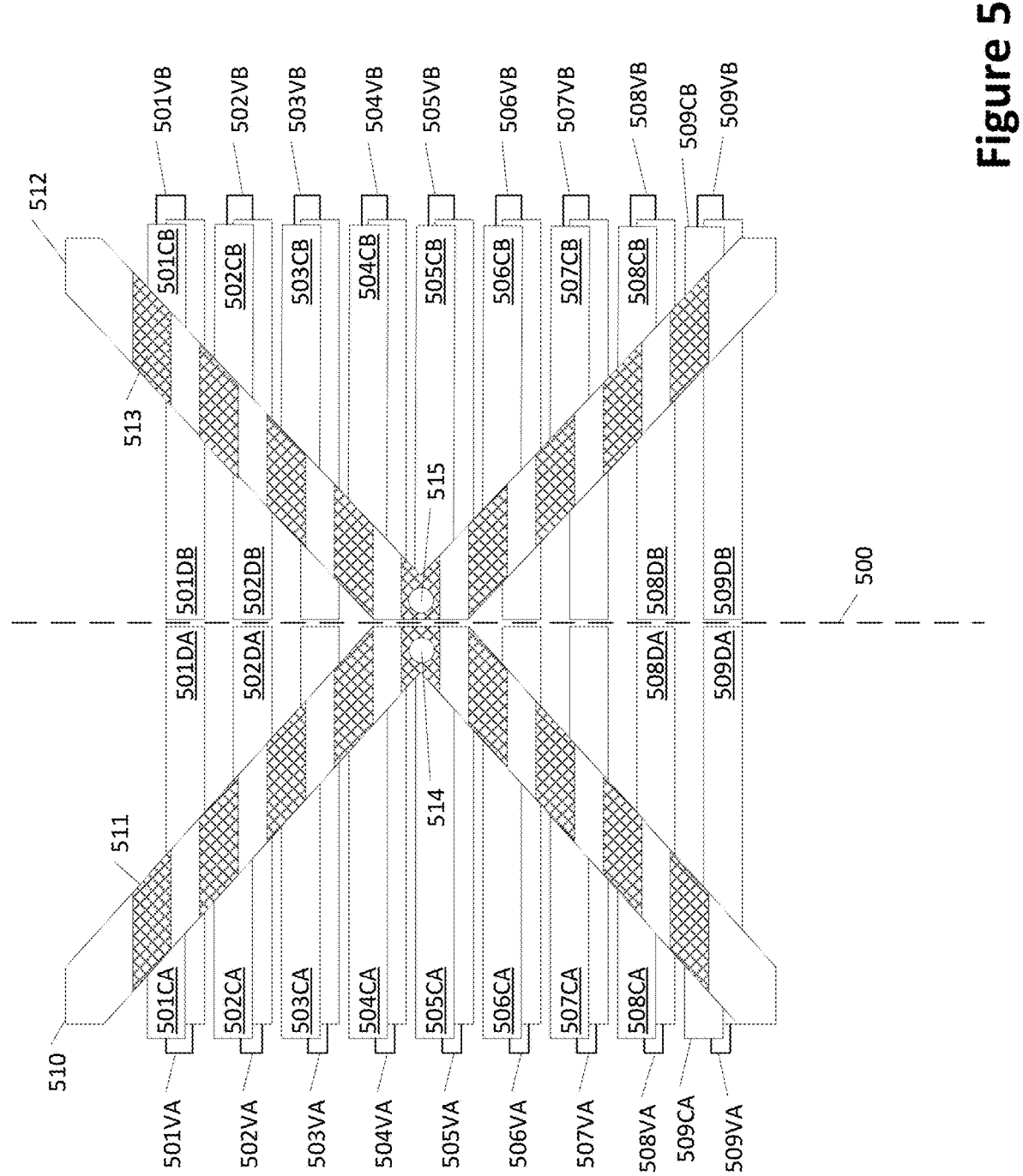
FIG. 5 shows an antenna with a feed conductor, a quantity of dipole elements, a quantity of intermediate conductors, and a quantity of electrical conductors.

FIG. 5 shows an example of an antenna. The antenna may comprise a plurality of dipole elements 501DA-509DA arranged on a first side of a centerline 500 and a corresponding plurality of dipole elements 501DB-509DB arranged on a second side of a centerline 500, with a gap separating each dipole pair. Each dipole element 501DA-509DA is connected to a respective electrical conductor 501VA-509VA. Each of the electrical conductors 501VA-509VA is connected to a respective intermediate conductor 501CA-509CA. Each of the intermediate conductors 501CA-509CA is capacitively coupled a portion (shown in a hatched region) of feed conductor 510. While FIG. 5 shows the hatched portions shifted toward the top of the figure, the shifting is to represent the stacking of the feed conductor 510 above the intermediate conductors 501CA-509CA, which are positioned above dipole elements 501DA-509DA. The feed conductor 510 may receive a signal at a location, for instance, at an upper end of the feed conductor 510 at the top of the figure, a lower end at the bottom of the figure, at location 514 in the middle of the feed conductor 510, or another location.

On the opposite side of centerline 500, a plurality of dipole elements 501DB-509DB are arranged opposite to dipole elements 501DA-509DA. Each of dipole elements 501DB-509DB is connected to a respective electrical conductor 501VB-509VB. Each of the electrical conductors 501VB-509VB is connected to a respective intermediate conductor 501CB-509CB. Each of the intermediate conductors 501CB-509CB is capacitively coupled to feed conductor 512 at a respective portion (shown in FIG. 5 as hatched portions 513 on the feed conductor 512). The feed conductor 512 may receive a signal at a location, for instance, at an upper end of the feed conductor 512 at the top of the figure, a lower end at the bottom of the figure, at location 515 in the middle of the feed conductor 512, or another location.

In FIG. 5, nine dipole pairs are shown. A greater or fewer quantity of pairs may be used of even or odd combinations (e.g., 2-100+ pairs).

Figure 6:
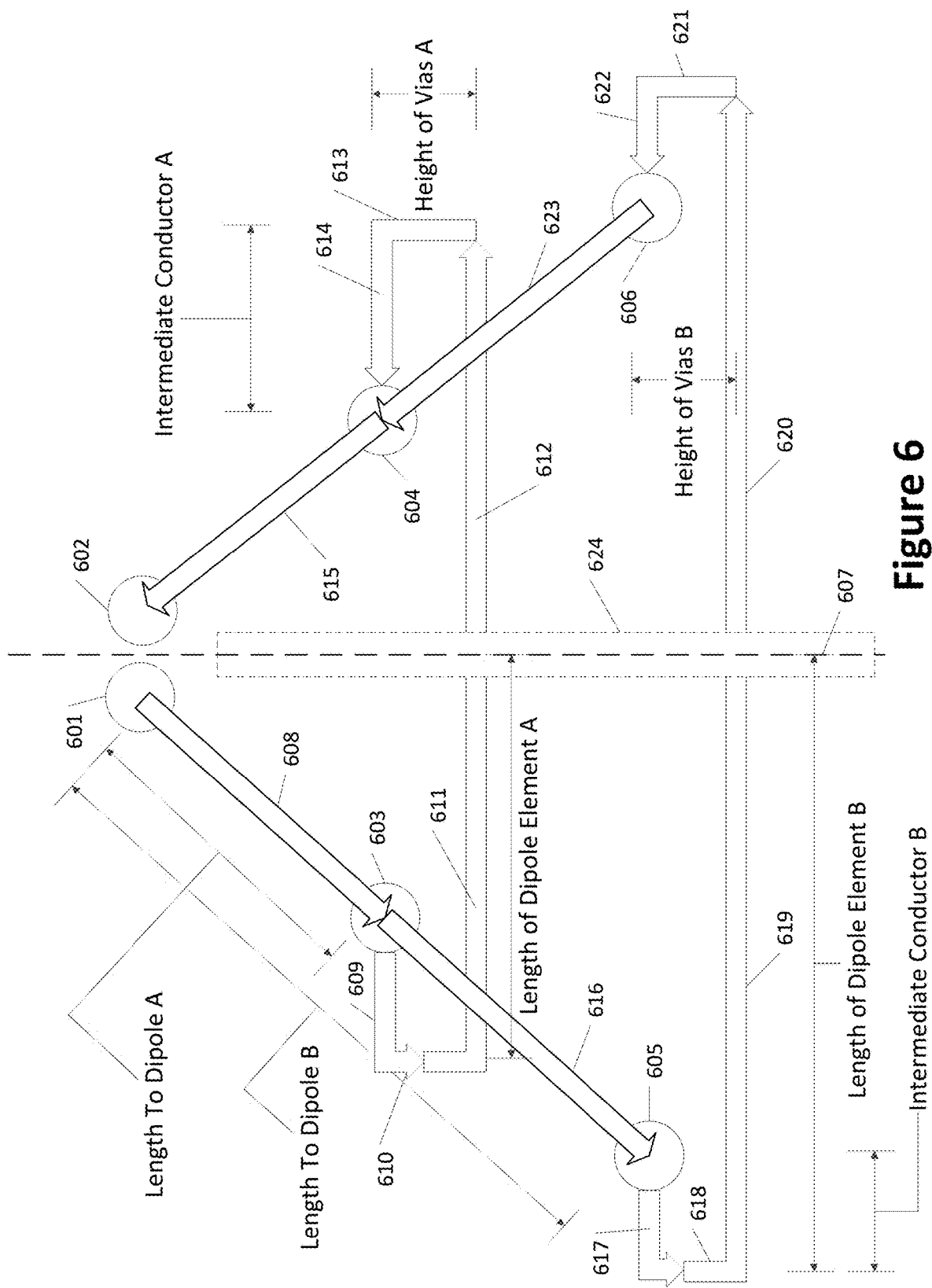
FIG. 6 shows two paths between the portions of the feed conductor layer, each path using a different dipole pair.

FIG. 6 shows an example of two paths between portions of the feed conductor (e.g., feed conductor 510 and feed conductor 512), each path using a different dipole pair. As the dimensions of elements on a left side of centerline 607 correspond to the dimensions on the right side of centerline 607, only one set of dimensions are identified.

FIG. 6 shows 6 locations 601-606. Locations 601, 603, and 605 are relative to a feed conductor on a left side of centerline 607 and locations 602, 604, and 606 are relative to a feed conductor on a right side of centerline 607. In the example of FIG. 6, a signal is received at location 601 and travels (represented by arrow 608) along the feed conductor to location 603. At location 603, a portion of the signal passes through a capacitive coupling to an intermediate conductor A, along (represented by arrow 609) an intermediate conductor A, along (represented by arrow 610) a via connecting intermediate conductor A to dipole element A, and along dipole element A to a gap 624. As the signal travels along (represented by arrow 611) the dipole element A on the left side of centerline 607, across the gap 624, and along (represented by arrow 612) a corresponding dipole element A on the right side of centerline 607, it forms a standing wave associated with dipole pairs driven at or near their resonant frequency. The signal travels along (represented by arrow 613) a via on the right side of centerline 607, along (represented by arrow 614) an intermediate conductor, across a capacitive coupling at location 604, and along (represented by arrow 615) another feed conductor to feed location 602. The total path length for the signal passing through locations 601-603-604-602 may be represented as the path lengths of arrows {608}+{the distance across the capacitive coupling at location 603}+{609}+{610}+{611}+ {the width of gap 624}+{612}+{613}+{614}+{the distance across the capacitive coupling at location 604}+{615}. Because the arrangement of FIG. 6 is symmetric about centerline 607, this length may be simplified to {the gap length 624}+2 x{608+609+610+611+the distance across the capacitive coupling at location 603}.

FIG. 6 also shows an additional signal path across gap 624. The signal is received at location 601 and travels (represented by arrow 608) along the feed conductor to location 603. At location 603, as described above, a portion of the signal passes through a capacitive coupling to the intermediate conductor A. The remaining portion of the signal continues along (represented by arrow 616) the feed conductor to location 605. At location 605, the signal passes through a capacitive coupling with an intermediate conductor B, along (represented by arrow 617) the intermediate conductor, along (represented by arrow 618) a via connecting intermediate conductor B to a dipole element B, and along (represented by arrow 619) dipole element B to the gap 624. As the signal travels along (represented by arrow 619) the dipole element B on the left side of centerline 607, across the gap 624, and along (represented by arrow 620) a corresponding dipole element B on the right side of centerline 607, it forms a standing wave associated with dipole pairs driven at or near their resonant frequency. The signal travels along (represented by arrow 621) a via on the right side of centerline 607, along (represented by arrow 622) an intermediate conductor, across a capacitive coupling at location 606, and along (represented by arrow 623) another feed conductor to location 604, then on to feed location 602. The total path length for the signal passing through locations 601-603-605-606-604-602 may be represented as the path lengths of arrows {608}+{616}+{the distance across the capacitive coupling at location 605}+{617}+{618}+{619}+ {the width of gap 624}+{620}+{621}+{622}+{the distance across the capacitive coupling at location 606}+{623}+ {615}. Because the arrangement of FIG. 6 is symmetric about centerline 607, this length may be simplified to {the gap length 624}+2 {608+609+610+611+the distance across the capacitive coupling at location 605}.

To adjust the phase of the portion of the signal passing between locations 603, 604 and the phase of the portion of the signal passing between locations 605, 606 to be the same when crossing gap 624, the path lengths identified in FIG. 6 may be modified.

Figure 7:
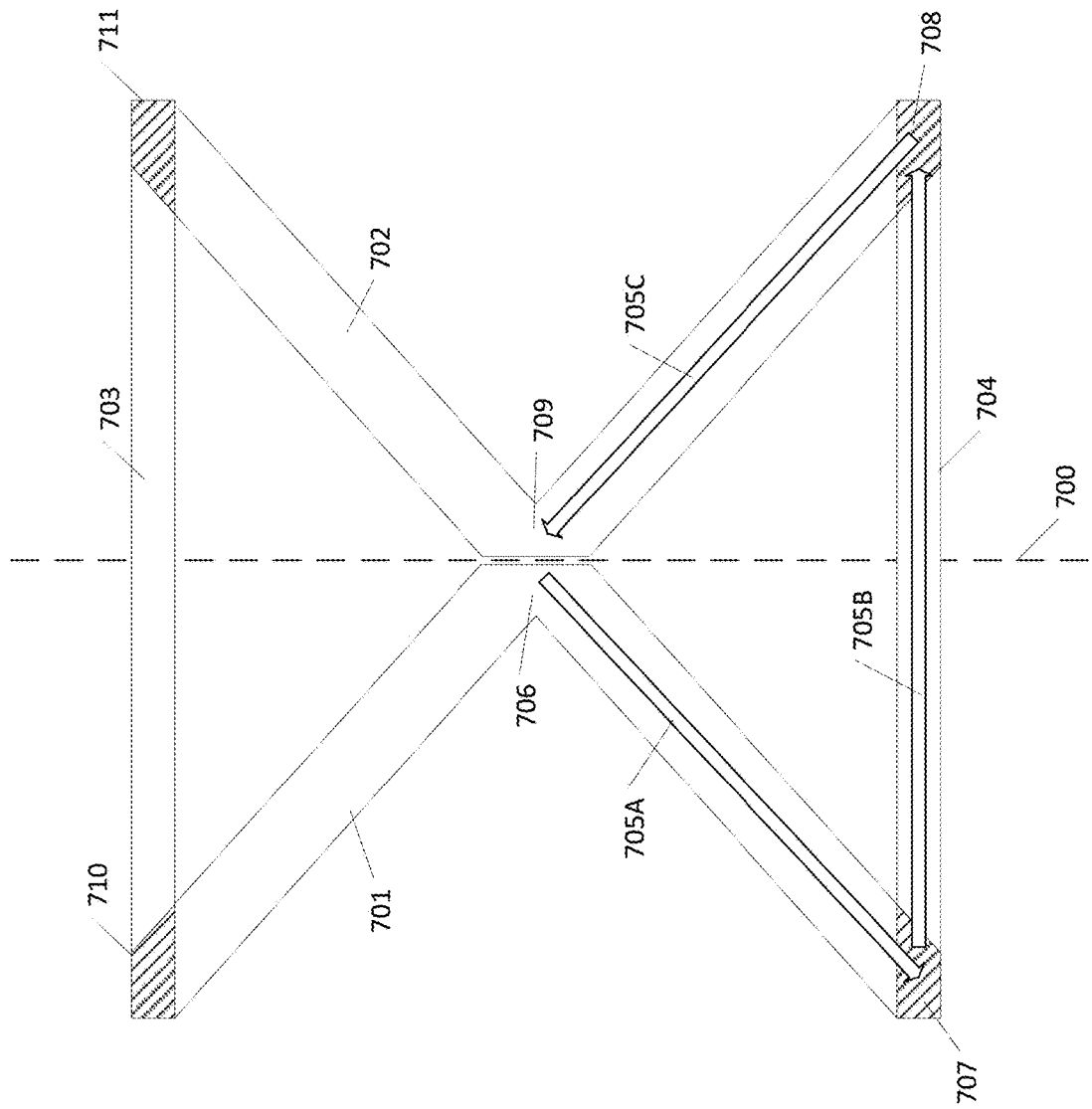
FIG. 7 shows the feed conductor portions connected by tuning loops.

The dipole array may further comprise loops as described with respect to FIG. 7. FIG. 7 shows a feed conductor 701 on a left side of a centerline 700 and a feed conductor 702 on a right side of the centerline 700. Feed conductors 701 and 702 may be connected by conductor 703 at locations 710 and 711, respectively. Also, feed conductors 701 and 702 may be connected by conductor 704 at locations 707 and 708, respectively. The conductors 703, 704 in combination with arms of feed conductors 701, 702 form loops. The conductors 703, 704 may be capacitively coupled to feed conductors 701 and 702. The loops formed by conductors 703, 704 may counter the increase in capacitance by increasing the inductance of the antenna. As such, the antenna may be tuned to improve its impedance (i.e., impedance matching to its environment). FIG. 7 shows, for instance, one loop with path lengths shown by arrow 705A (from a feed location to a connection location 707 between feed conductor 701 and conductor 704), arrow 705B (from the connection location 707 to connection location 708, where conductor 704 may be connected to feed conductor 702), and arrow 705C (from the connection location 708 to a feed location 709). By extending the path lengths 705A, 705B, and 705C, the impedance of each loop, and the overall antenna, may be adjusted. In addition to adjusting the impedance, the position of the loops may help focus the antenna's near field signal below the antenna while reducing the antenna's signal on the sides of the antenna (e.g., toward the top and bottom of FIG. 7). For example, by adjusting the phase of the signal to be out of phase, when crossing the centerline 700, with an adjacent dipole pair, the out-of-phase signal from the loops may destructively interfere with the in-phase signal or signals from the dipole elements, thereby reducing the in-phase signal outside the loop sides of the antenna.

Figure 8:
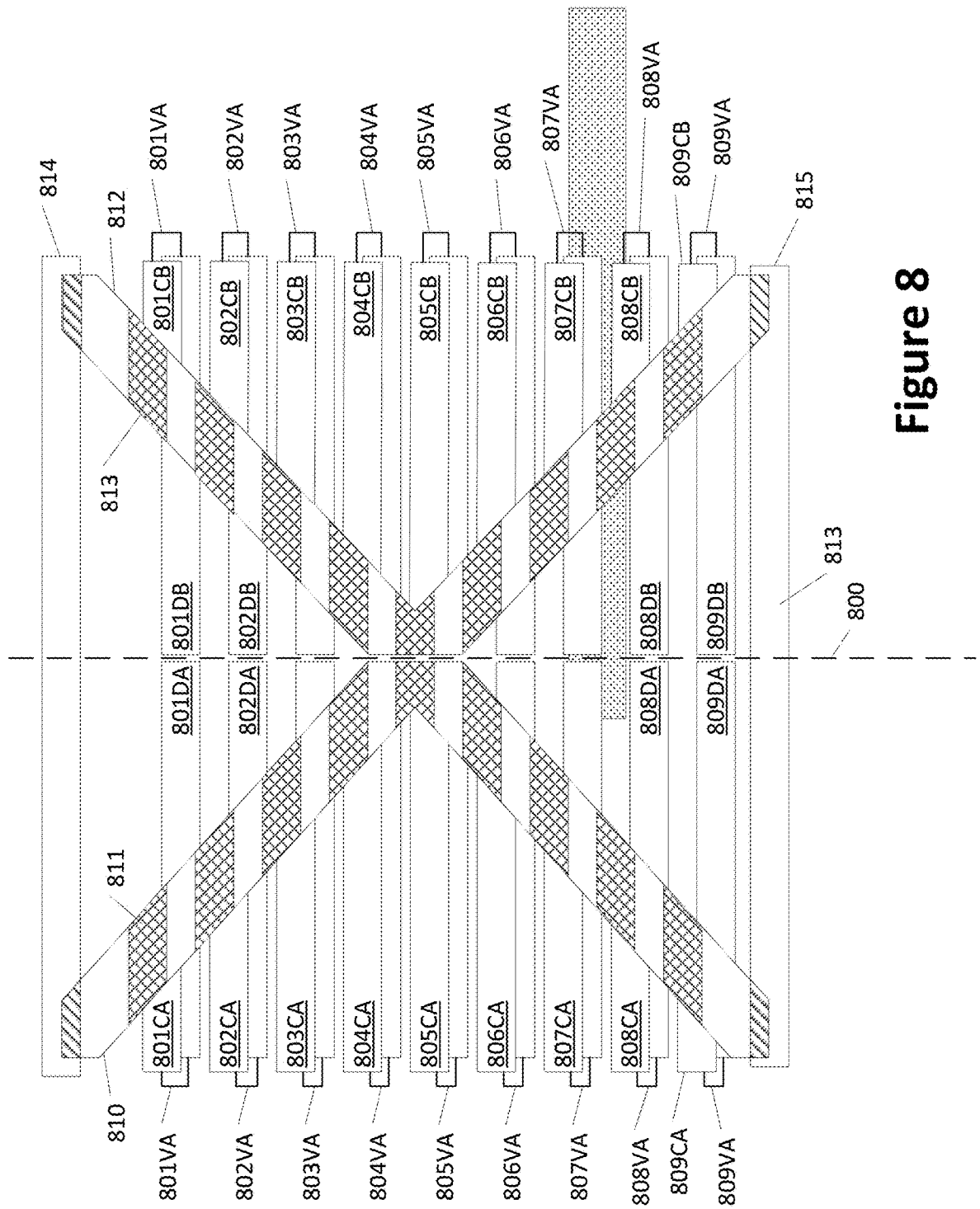
FIG. 8 shows a dipole array, a conductive layer, and a feed conductor layer.

FIG. 8 shows a dipole array, a conductive layer, and a feed conductor layer. FIG. 8 shows the combination of the antenna of FIG. 5 with the loops of FIG. 7. The antenna may comprise a plurality of dipole elements 801DA-809DA arranged on a first side of a centerline 800 and a corresponding plurality of dipole elements 801DB-809DB arranged on a second side of a centerline 800, with a gap separating each dipole pair. Each dipole element 801DA-809DA is connected to a respective electrical conductor 801VA-809VA. Each of the electrical conductors 801VA-809VA is connected to a respective intermediate conductor 801CA-809CA. Each of the intermediate conductors 801CA-809CA is capacitively coupled to a portion (shown in a hatched region) of feed conductor 810. While FIG. 8 shows the hatched portions shifted toward the top of the figure, the shifting is to represent the stacking of the feed conductor 810 above the intermediate conductors 801CA-809CA, which are positioned above dipole elements 801DA-809DA. The feed conductor 810 may receive a signal at a location, for instance, at an upper end of the feed conductor 810 at the top of the figure, a lower end at the bottom of the figure, at location in the middle of the feed conductor 810, or another location.

On the opposite side of centerline 800, a plurality of dipole elements 801DB-809DB are arranged opposite to dipole elements 801DA-809DA. Each of dipole elements 801DB-809DB is connected to a respective electrical conductor 801VB-809VB. Each of the electrical conductors 801VB-809VB is connected to a respective intermediate conductor 801CB-809CB. Each of the intermediate conductors 801CB-809CB is capacitively coupled to feed conductor 812 at a respective portion (shown in FIG. 8 as hatched portions 813 on the feed conductor 812). The feed conductor 812 may receive a signal at a location, for instance, at an upper end of the feed conductor 812 at the top of the figure, a lower end at the bottom of the figure, at location 815 in the middle of the feed conductor 812, or another location. FIG. 8 also includes conductors 814 and 815, connected at or near ends of feed conductors 810 and 812.

In FIG. 8, nine dipole pairs are shown. A greater or fewer quantity of pairs may be used of even or odd combinations (e.g., 2-100+pairs). FIG. 9A shows a dipole array with nine dipole element pairs 901A-909A on one side and 901B-909B on the other side, with the 901A/901B dipole pair next to conductor 910 and the 909A/909B dipole pair next to conductor 911. FIG. 9B shows a dipole array with 18 dipole pairs. Specifically, FIG. 9B shows a dipole array with 18 dipole element pairs 912A-929A on one side and 912B-929B on the other side, with the 912A/912B dipole pair next to conductor 930 and the 929A/929B dipole pair next to conductor 931.

In some examples, the dipole elements, where distinct from the electrical conductors, may have a common length. For instance, in FIGS. 9A and 9B, the dipole elements 901A-909A, 901B-901B, 912A-929A, 912B-929B may have a common length. In other examples, the dipole elements may have different lengths.

For purposes of explanation with respect to FIGS. 10A-10F, dipole elements and intermediate conductors are referred to as having proximate and distal ends relative to a centerline 1000.

Figures 10A, 10B:
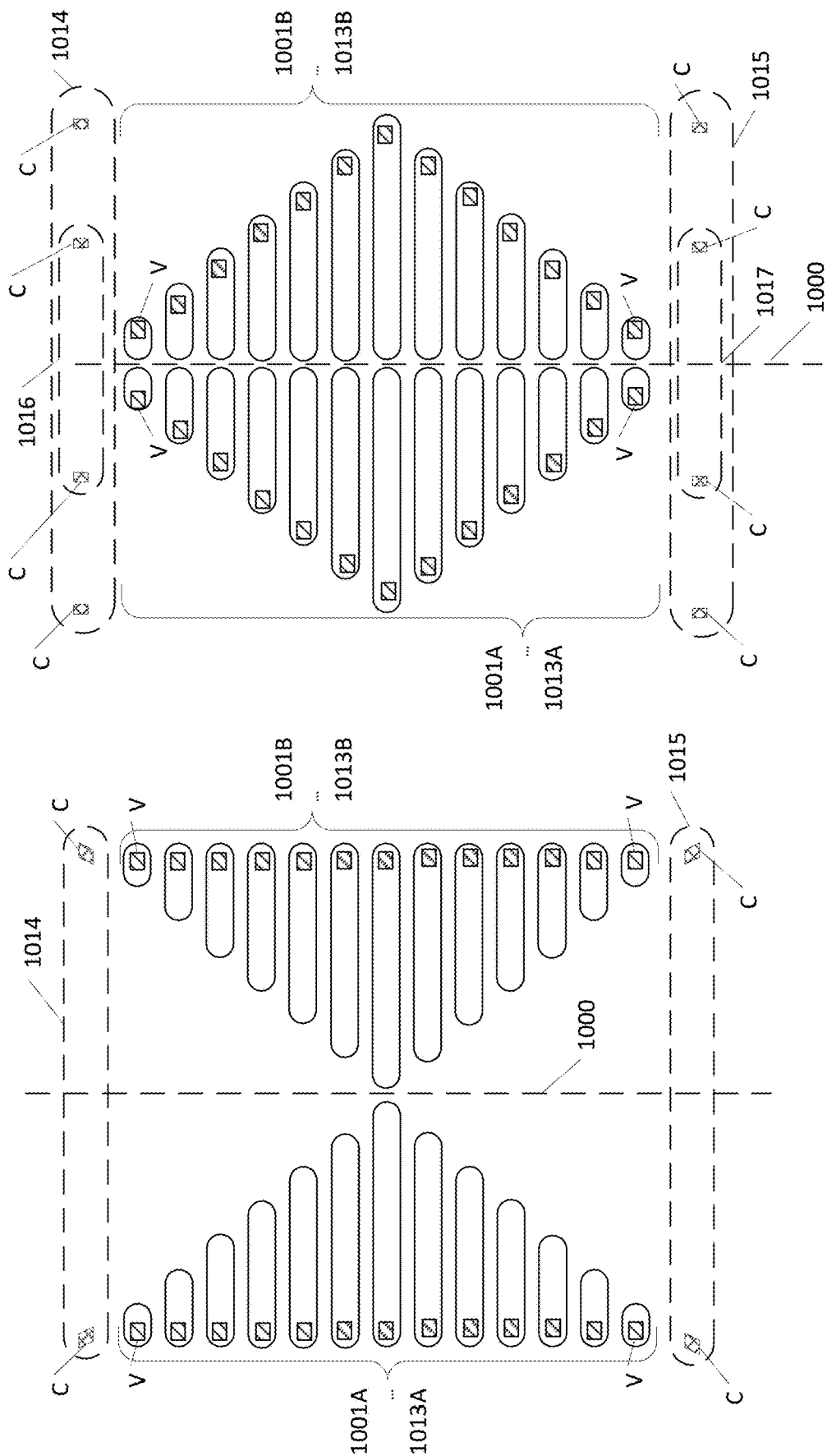
FIG. 10A shows a dipole array with dipole pairs of different lengths.
FIG. 10B shows another dipole array with dipole pairs of different lengths.

FIG. 10A shows a dipole array with dipole pairs of different lengths. Dipole elements 1001A-1013A and dipole elements 1001B-1013B may be positioned with their distal ends at a common distance from centerline 1000 while their proximate ends vary in distance from centerline 1000. In FIG. 10A, the proximate ends of dipoles 1001A, 1001B, 1013A, and 1013B are farthest from the centerline 1000, the proximate ends of dipole elements 1007A and 1007B are closest to the centerline 1000, and the remaining dipole elements' proximate ends increase in distance away from the centerline as the distance increases from dipole elements 1007A and 1007B. The connections of the dipole elements to electrical conductors are identified by vias V. FIG. 10A also shows conductors 1014 and 1015 with capacitive coupling regions C connected to feed conductors (not shown).

FIG. 10B shows another dipole array with dipole pairs of different lengths. Dipole elements 1001A-1013A and dipole elements 1001B-1013B may be positioned with their proximate ends at a common distance from centerline 1000 while their distal ends vary in distance from centerline 1000. In FIG. 10B, the distal ends of dipoles 1001A, 1001B, 1013A, and 1013B are closest to the centerline 1000, the distal ends of dipole elements 1007A and 1007B are farthest from the centerline 1000, and the remaining dipole elements' distal ends decrease in distance from centerline 1000 as distance increases from dipole elements 1007A and 1007B. The connections of the dipole elements to electrical conductors are identified by vias V. FIG. 10B also shows conductors 1014 and 1015 with capacitive coupling regions C connected to feed conductors (not shown). Further, as the shape of the feed conductors may be of any shape, the length of conductors 1014, 1015 may be adjusted to tune the impedance of the antenna (shown by shorter conductors 1016 and 1017).

FIG. 10C shows a first example of intermediate conductors of different lengths. Intermediate conductors 1021A-1033A and intermediate conductors 1021B-1033B may be positioned with their distal ends at a common distance from centerline 1000 while their proximate ends vary in distance from centerline 1000. In FIG. 10C, the proximate ends of intermediate conductors 1021A, 1021B, 1033A, and 1033B are farthest from the centerline 1000, the proximate ends of intermediate conductors 1027A and 1027B are closest to the centerline 1000, and the remaining intermediate conductors' proximate ends increase in distance away from the centerline as the distance increases from intermediate conductors 1027A and 1027B. The connections of the intermediate conductors to electrical conductors are identified by vias V. The capacitive couplings of the intermediate conductors to feed conductors (not shown) are identified by regions C. FIG. 10C also shows conductors 1014 and 1015 with capacitive coupling regions C connected to feed conductors (not shown).

FIG. 10D shows a second example of intermediate conductors of different lengths. Intermediate conductors 1021A-1033A and intermediate conductors 1021B-1033B may be positioned with their proximate ends at a common distance from centerline 1000 while their distal ends vary in distance from centerline 1000. In FIG. 10D, the distal ends of intermediate conductors 1021A, 1021B, 1033A, and 1033B are closest to the centerline 1000, the distal ends of intermediate conductors 1027A and 1027B are farthest from the centerline 1000, and the remaining intermediate conductors' distal ends decrease in distance from centerline 1000 as distance increases from intermediate conductors 1027A and 1027B. The connections of the intermediate conductors to electrical conductors are identified by vias V. The capacitive couplings of the intermediate conductors to feed conductors (not shown) are identified by regions C. FIG. 10D also shows conductors 1014 and 1015 with capacitive coupling regions C connected to feed conductors (not shown). Further, as the shape of the feed conductors may be of any shape, the length of conductors 1014, 1015 may be adjusted to tune the impedance of the antenna (shown by shorter conductors 1016 and 1017).

Figures 10E, 10F:
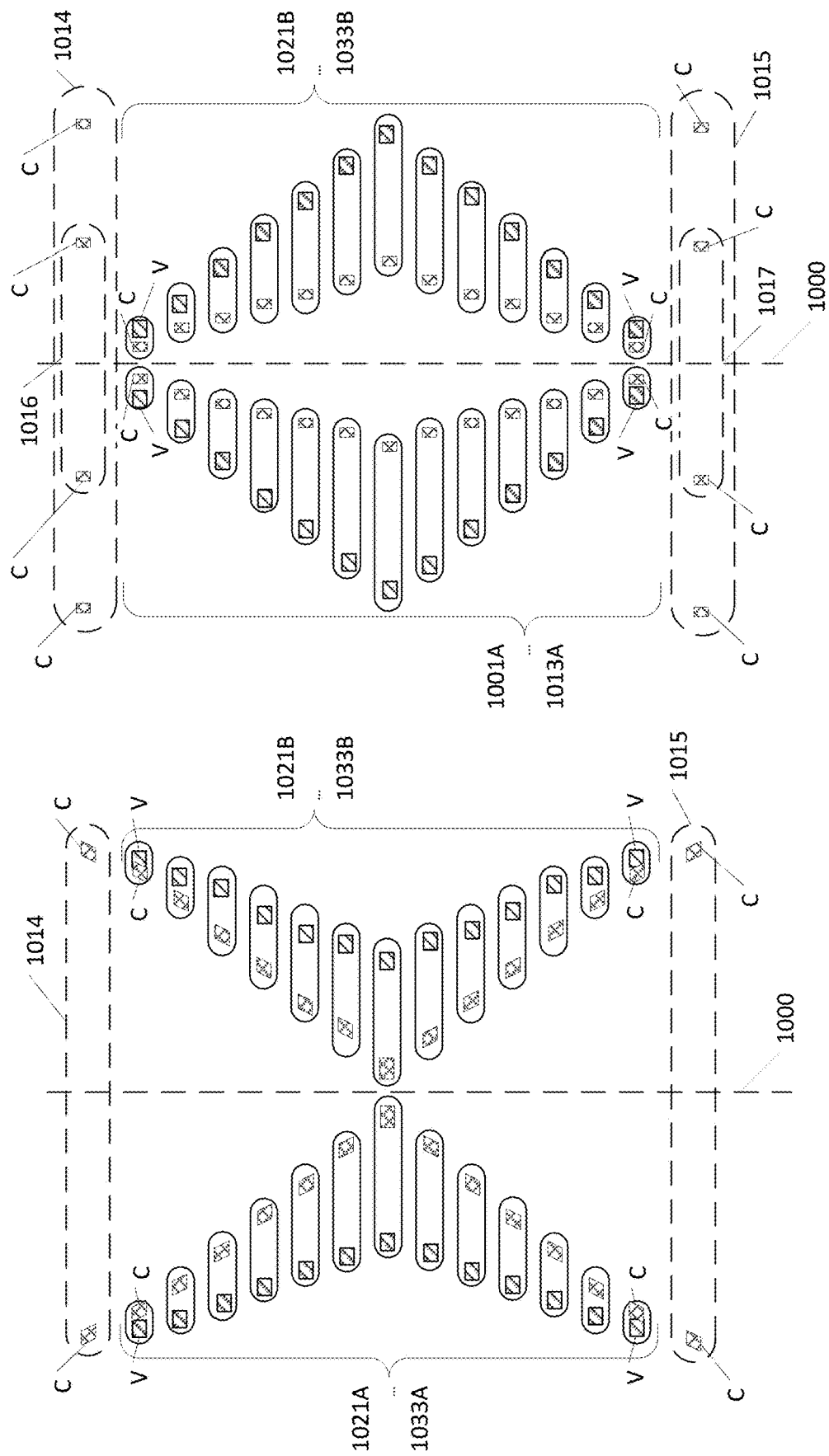
FIG. 10E shows a third example of intermediate conductors of different lengths.
FIG. 10F shows a fourth example of intermediate conductors of different lengths.

FIG. 10E shows a third example of intermediate conductors of different lengths. The proximate ends of the intermediate conductors 1021A-1033A and 1021B-1033B vary instance from the centerline 1000 as described in FIG. 10C. The distal ends of intermediate conductors 1027A and 1027B are closest to centerline 1000. The distal ends of the remaining intermediate conductors increase in distance from centerline 1000 but at a decreased rate of that compared to the rate of change of the distance of their proximate ends to the centerline 1000. The effect is that intermediate conductors 1027A and 1027B have the greatest length while intermediate conductors 1021A, 1021B, 1033A, and 1033B have the shortest length.

FIG. 10F shows a fourth example of intermediate conductors of different lengths. The distal ends of the intermediate conductors 1021A-1033A and 1021B-1033B vary instance from the centerline 1000 as described in FIG. 10D. The proximate ends of the intermediate conductors 1027A and 1027B are farthest from centerline 1000. The proximate ends of the remaining intermediate conductors decrease in distance from centerline 1000 but at a decreased rate of that compared to the rate of change of the distance of their distal ends to the centerline 1000. The effect is that intermediate conductors 1027A and 1027B have the greatest length while intermediate conductors 1021A, 1021B, 1033A, and 1033B have the shortest length.

FIG. 10G shows a fifth example of intermediate conductors of different lengths. The proximate ends and the distal ends of the intermediate conductors 1021A-1033A and 1021B-1033B vary instance from the centerline 1000 as described in FIG. 10E but with the rates of change reversed. The effect is that intermediate conductors 1027A and 1027B have the shortest length while intermediate conductors 1021A, 1021B, 1033A, and 1033B have the longest length.

FIG. 10H shows a sixth example of intermediate conductors of different lengths. The proximate ends and the distal ends of the intermediate conductors 1021A-1033A and 1021B-1033B vary instance from the centerline 1000 as described in FIG. 10F but with the rates of change reversed. The effect is that intermediate conductors 1027A and 1027B have the shortest length while intermediate conductors 1021A, 1021B, 1033A, and 1033B have the longest length.

Figures 11A, 11B:
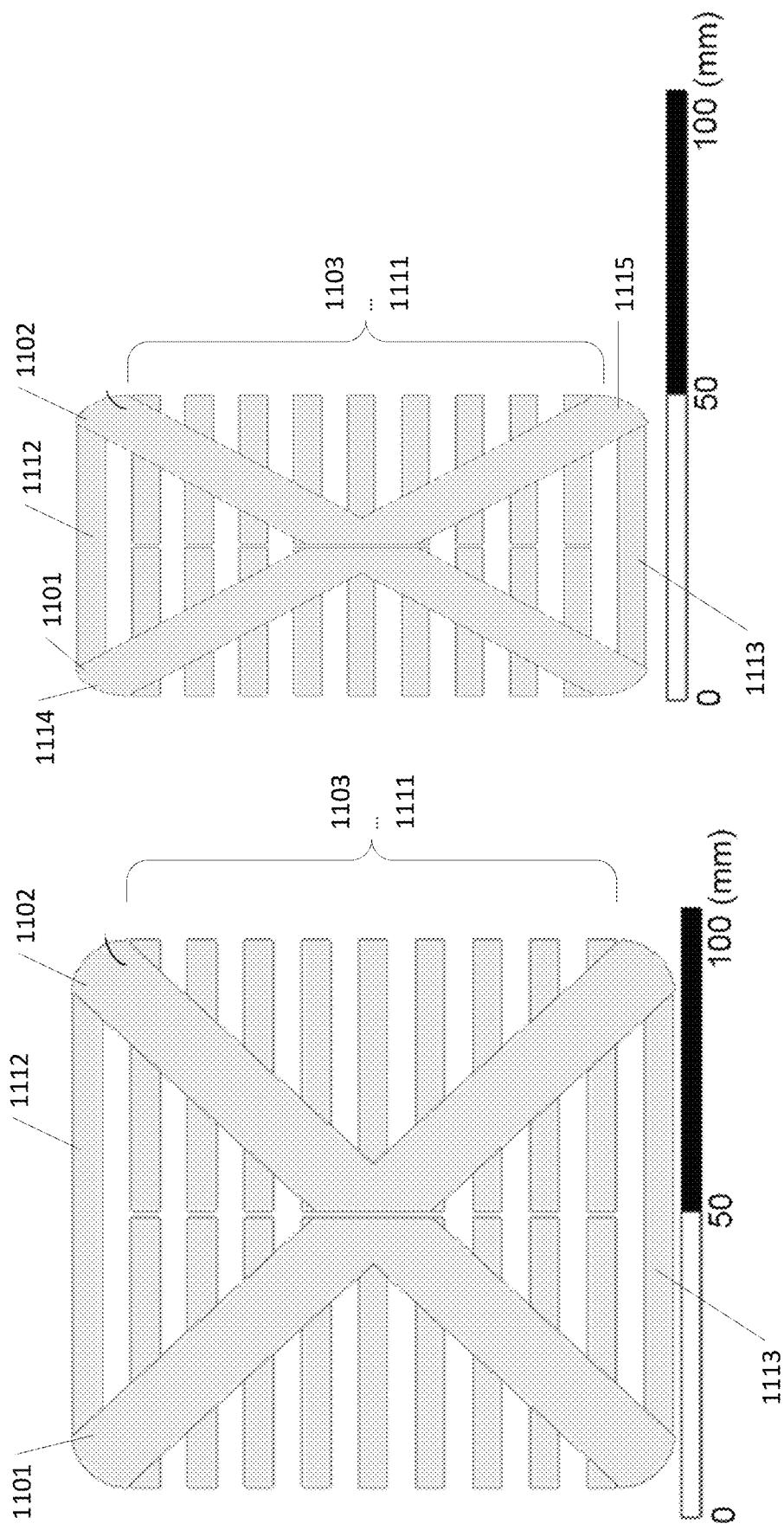
FIG. 11A shows an antenna with a feed conductor layer.
FIG. 11B shows an antenna with a feed conductor layer having at least one smaller dimension than that of the antenna of FIG. 11A.

In some situations, a narrower antenna may be desired, for example, shrinking the dimension of the dipole array in a direction perpendicular to a centerline. For example, FIG. 11A shows an antenna of a first dimension in a direction perpendicular to a centerline. FIG. 11B shows an antenna with a feed conductor layer having at least one smaller dimension than that of the antenna of FIG. 11A. FIG. 12A shows another antenna. FIG. 12B shows another antenna having at least one smaller dimension than that of the antenna of FIG. 12A. FIG. 13A shows yet another antenna. FIG. 13B shows yet another antenna having at least one smaller dimension than that of the antenna of FIG. 13A.

Figure 14:
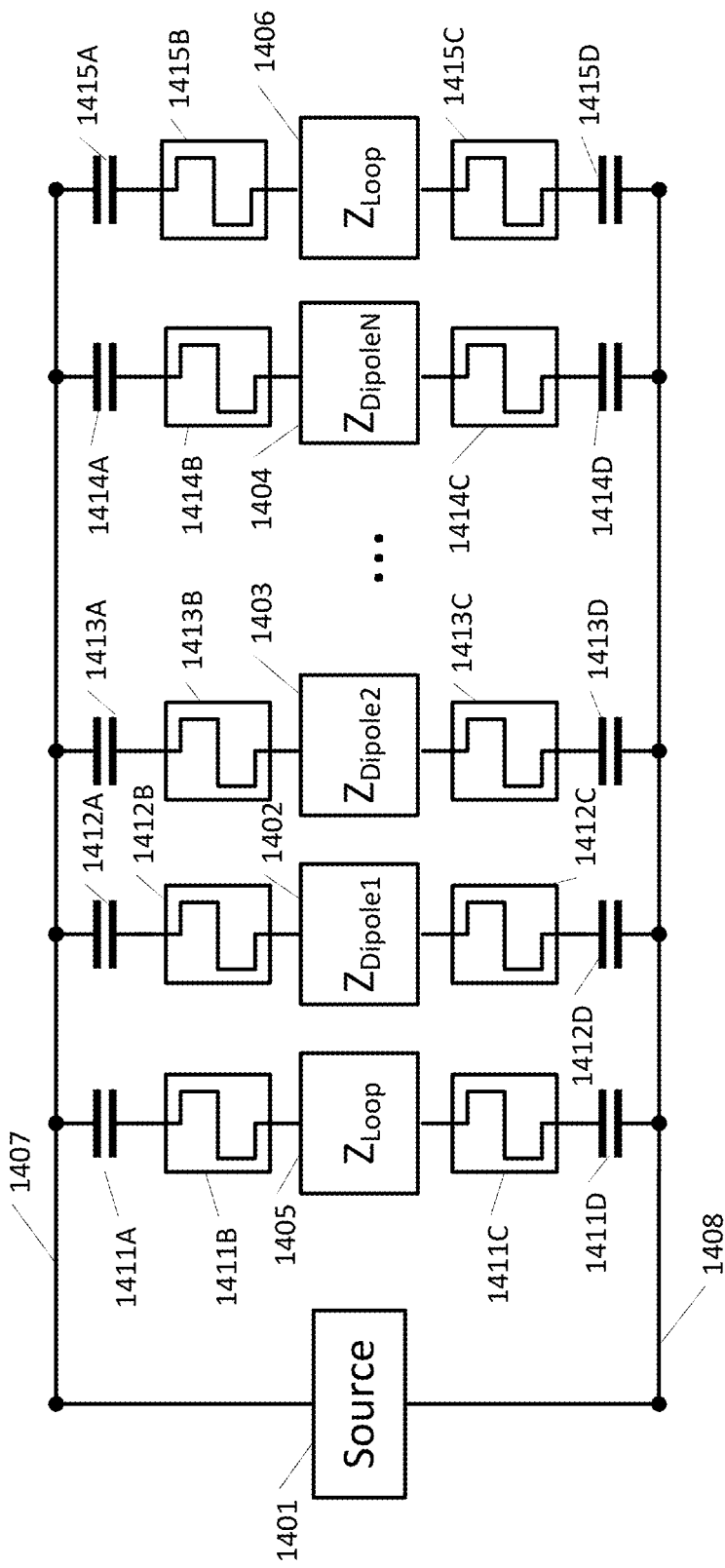
FIG. 14 shows an example of a simplified equivalent circuit model for an antenna with a conductive layer and a feed conductor layer.

FIG. 14 shows an example of a simplified equivalent circuit model for an antenna with intermediate conductors and feed conductors. The circuit includes a source 1401, a quantity of dipole pairs $Z_{Dipole1}$ 1402, $Z_{Dipole2}$ 1403, through $Z_{DipoleN}$ 1404, and two tuning loops $Z_{Loop}$ 1405 and $Z_{Loop}$ 1406. The dipole pairs and the loops are connected between a first feed conductor 1407 and a second feed conductor 1408. The dipoles and loops are connected in parallel with each other. Intermediate conductors (and possible electrical conductors—e.g., vias) are represented as elements 1411B, 1411C, 1412B, 1412C, 1413B, 1413C, 1414B, 1414C, 1415B, and 1415C. For explanatory purposes, the intermediate conductors and possible electrical conductors are collectively referred to as path length adjustors. For example, for the $Z_{Loop}$ 1405, the capacitive connection between the feed conductor 1407 and the path length adjustor 1411B is represented by a capacitor 1411A. Similarly, the capacitive connection between the feed conductor 1408 and the path length adjustor 1411C is represented by a capacitor 1411D. For the $Z_{Loop}$ 1406, the capacitive connection between the feed conductor 1407 and the path length adjustor 1415B is represented by a capacitor 1415A. Similarly, the capacitive connection between the feed conductor 1408 and the path length adjustor 1415C is represented by a capacitor 1415D. For the $Z_{Dipole1}$ 1402, a capacitive connection between the feed conductor 1407 and the path length adjustor 1412B is represented by capacitor 1412A. Similarly, a capacitive connection between the feed conductor 1408 and the path length adjustor 1412C is represented by capacitor 1412D. For the $Z_{Dipole2}$ 1403, a capacitive connection between the feed conductor 1407 and the path length adjustor 1413B is represented by capacitor 1413A. Similarly, a capacitive connection between the feed conductor 1408 and the path length adjustor 1413C is represented by capacitor 1413D. For the $Z_{DipoleN}$ 1404, a capacitive connection between the feed conductor 1407 and the path length adjustor 1414B is represented by capacitor 1414A. Similarly, a capacitive connection between the feed conductor 1408 and the path length adjustor 1414C is represented by a capacitor 1414D.

Figure 15:
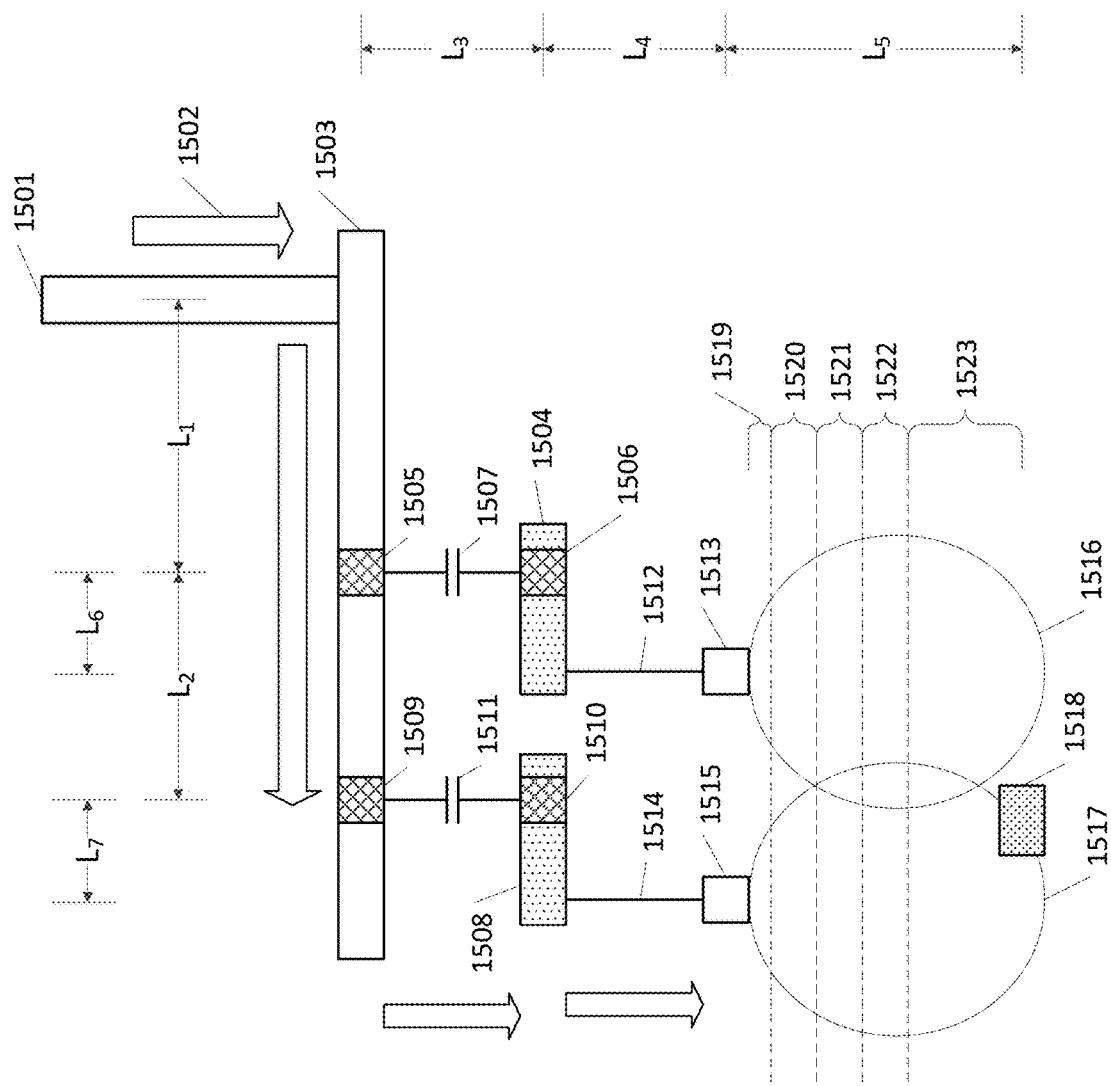
FIG. 15 shows an elevation view of two dipole elements connected to one or more conductive layers with a distance between the connections and capacitive couplings to a feed conductor.

FIG. 15 shows an elevation view of two dipole elements connected to one or more conductive layers with a distance between the connections and capacitive couplings to a feed conductor. A radiofrequency feed connector 1501 provides a signal 1502 to a feed conductor 1503. The signal travels along the feed conductor 1503. An intermediate conductor 1504 is capacitively coupled (represented by capacitor 1507) with the feed conductor 1503 between location 1506 of the intermediate conductor 1504 and location 1505 of the feed conductor 1503. Also, an intermediate conductor 1508 is capacitively coupled (represented by capacitor 1511) with the feed conductor 1503 between location 1510 of the intermediate conductor 1508 and location 1509 of the feed conductor 1503. A first portion of the signal continues to the first intermediate conductor 1504 and a second portion of the signal continues to the second intermediate conductor 1508. The first portion of the signal travels along an electrical conductor 1512 to a first dipole element 1513 and is transmitted, as radiation pattern 1516, to an implanted stimulator 1518. The second portion of the signal travels along an electrical conductor 1514 to a second dipole element 1515 and is transmitted, as radiation pattern 1517, to the implanted stimulator 1518. FIG. 15 also shows various substances the radiation patterns 1516 and 1517 may encounter before reaching the implanted stimulator 1518 including one or more of a gap 1519 (e.g., air, an adhesive, a gel, or the like), one or more layers of skin 1520, subcutaneous fat 1521, blood vessels 1522, or body tissue 1523 (e.g., muscle fibers, nerves, and the like).

FIG. 15 identifies various path lengths including $L_1$ (a distance from a feed location on feed conductor 1503 to the first capacitive coupling location 1505), $L_2$ (a distance from the first capacitive coupling location 1505 to the second capacitive coupling location 1509), $L_3$ (a distance from the feed conductor 1503 to the intermediate conductors 1504 and 1508), $L_4$ (a distance from the intermediate conductors 1504 and 1508 to a plane of the first dipole element 1513 and the second dipole element 1515), $L_5$ (a distance from the plane of the first dipole element 1513 and the second dipole element 1515 to the implanted stimulator 1518), $L_6$ (a length of the intermediate conductor 1604 from the capacitive coupling location 1606 to the electrical conductor 1612), and $L_7$ (a length of the intermediate conductor 1608 from the capacitive coupling location 1610 to the electrical conductor 1614).

The total path length from a feed location on the feed conductor 1603 to the first dipole element 1613 may be expressed as follows:

$$L_{FirstDipole} = L_1 + L_3 + L_6 + L_4 \quad (3)$$

The total path length from a feed location on the feed conductor 1603 to the second dipole element 1615 may be expressed as follows:

$$L_{SecondDipole} = L_1 + L_2 + L_3 + L_7 + L_4 \quad (4)$$

Figure 16:
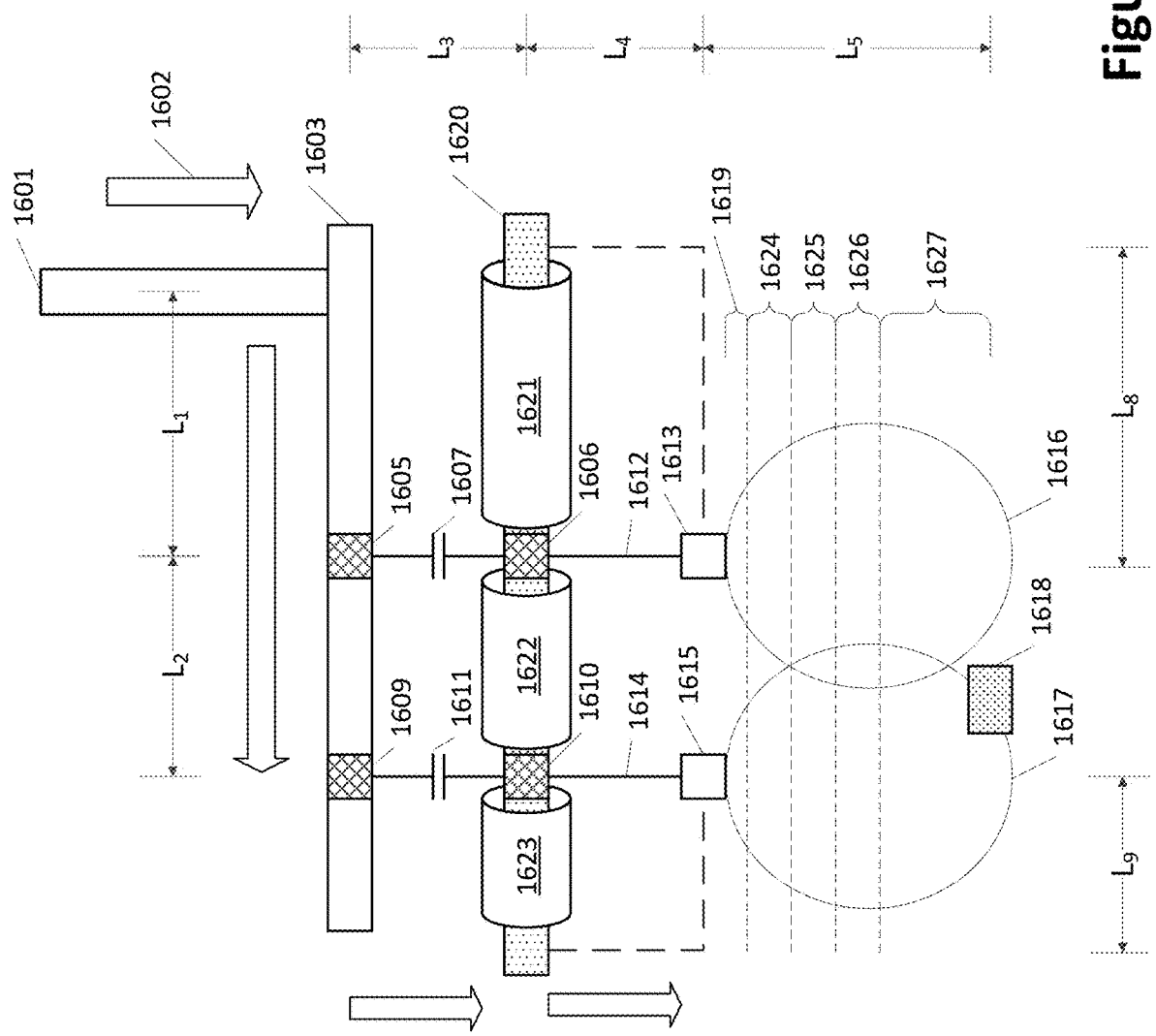
FIG. 16 shows an elevation view of two dipole elements connected to a partially shielded conductive layer.

FIG. 16 shows an elevation view of two dipole elements connected to a partially shielded conductive layer. A radiofrequency connector 1601 provides a signal 1602 to a feed conductor 1603. The signal travels along the feed conductor 1603. An intermediate conductor 1620 is capacitively coupled (represented by capacitor 1607) with the feed conductor 1603 between location 1606 of the intermediate conductor 1620 and location 1605 of the feed conductor 1603. Also, the intermediate conductor 1620 is capacitively coupled (represented by capacitor 1611) with the feed conductor 1603 between location 1610 of the intermediate conductor 1620 and location 1609 of the feed conductor 1603. A first portion of the signal continues to the intermediate conductor 1620 via the capacitive coupling 1607 and a second portion of the signal continues to the intermediate conductor 1620 via the capacitive coupling 1611. At least some of the first portion of the signal travels along an electrical conductor 1612 to a first dipole element 1613 and is transmitted, as radiation pattern 1616, to an implanted stimulator 1618. At least some of the second portion of the signal travels along an electrical conductor 1614 to a second dipole element 1615 and is transmitted, as radiation pattern 1617, to the implanted stimulator 1618. Portions of the intermediate conductor 1620 may be shielded from additional capacitive coupling with metal or metalized layers 1621, 1622, and 1623, located between exposed portions of the intermediate conductor 1620.

As the intermediate conductor 1620 extends between locations 1606 and 1610, some of at least one of the first portion of the signal or the second portion of the signal may travel between these locations, for example, based on the impedance of the components of the antenna. The impedance of the antenna of FIG. 16 and the antennas of the figures may change based on the location of an implanted stimulator relative to one or more of the antennas and/or other factors including how planar the dipole array is on a wearer's skin, the consistency of tissues and other structures between the antenna and the implanted stimulator, or a relative angle or rotation between axes of an antenna of the implanted stimulator and the relative position or orientation of the antenna.

FIG. 16 also shows various substances the radiation patterns 1616 and 1617 may encounter before reaching the implanted stimulator 1618 including one or more of a gap 1619 (e.g., air, an adhesive, a gel, or the like), one or more layers of skin 1624, subcutaneous fat 1625, blood vessels 1626, or body tissue 1627 (e.g., muscle fibers, nerves, and the like).

FIG. 16 identifies various path lengths including $L_1$ (a distance from a feed location on feed conductor 1603 to the first capacitive coupling location 1605), $L_2$ (a distance from the first capacitive coupling location 1605 to the second capacitive coupling location 1609), $L_3$ (a distance from the feed conductor 1603 to the intermediate conductor 1620), $L_4$ (a distance from the intermediate conductor 1620 to a plane of the first dipole element 1613 and the second dipole element 1615), and $L_5$ (a distance from the plane of the first dipole element 1613 and the second dipole element 1615 to the implanted stimulator 1618).

Alternatively or additionally, the first dipole element 1613 may be connected to a different portion of the intermediate conductor 1620 as shown by a dashed line connecting to a portion of the intermediate conductor 1620 to the right of shield 1621. In that situation, an additional length $L_8$ (a length shown in the dashed line from the intermediate conductor 1620 to the first dipole element 1613) may be determined. Alternatively or additionally, the second dipole element 1615 may be connected to a different portion of the intermediate conductor 1620 as shown by a dashed line connecting to a portion of the intermediate conductor 1620 to the left of shield 1623. In that situation, an additional length $L_9$ (a length shown in the dashed line from the intermediate conductor 1620 to the second dipole element 1615) may also be determined.

The total path length from a feed location on the feed conductor 1603 to the first dipole element 1613 (using the dashed line connection path) may be expressed as follows:

$$L_{FirstDipole} = L_1 + L_3 + L_4 + 2(L_8) \tag{5}$$

The total path length from a feed location on the feed conductor 1603 to the second dipole element 1615 (using the dashed line connection path) may be expressed as follows:

$$L_{SecondDipole} = L_1 + L_2 + L_3 + L_4 + 2(L_9) \tag{6}$$

Figure 17:
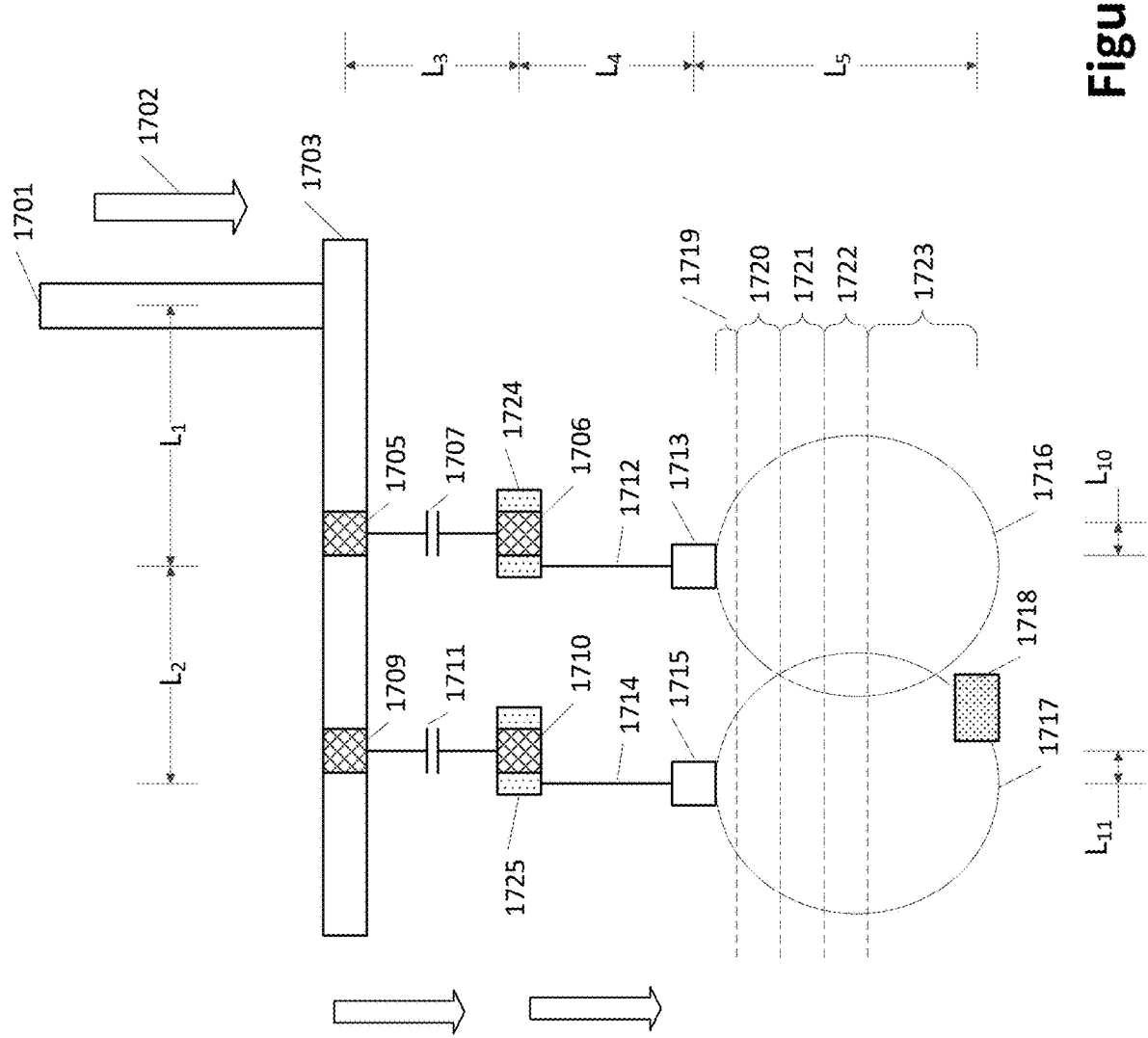
FIG. 17 shows an elevation view of two dipole elements connected to one or more conductive layers with a short distance between the connections and capacitive couplings to a feed conductor.

FIG. 17 shows an elevation view of two dipole elements connected to one or more conductive layers with a short distance between the connections and capacitive couplings to a feed conductor. A radiofrequency connector 1701 provides a signal 1702 to a feed conductor 1703. The signal travels along the feed conductor 1703. An intermediate conductor 1724 is capacitively coupled (represented by capacitor 1707) with the feed conductor 1703 between location 1706 of the intermediate conductor 1724 and location 1705 of the feed conductor 1703. Also, an intermediate conductor 1725 is capacitively coupled (represented by capacitor 1711) with the feed conductor 1703 between location 1710 of the intermediate conductor 1725 and location 1709 of the feed conductor 1703. A first portion of the signal continues to the first intermediate conductor 1724 and a second portion of the signal continues to the second intermediate conductor 1725. The first portion of the signal travels along an electrical conductor 1712 to a first dipole element 1713 and is transmitted, as radiation pattern 1716, to an implanted stimulator 1718. The second portion of the signal travels along an electrical conductor 1714 to a second dipole element 1715 and is transmitted, as radiation pattern 1717, to the implanted stimulator 1718. FIG. 17 also shows various substances the radiation patterns 1716 and 1717 may encounter before reaching the implanted stimulator 1718 including one or more of a gap 1719 (e.g., air, an adhesive, a gel, or the like), one or more layers of skin 1720, subcutaneous fat 1721, blood vessels 1722, or body tissue 1723 (e.g., muscle fibers, nerves, and the like).

FIG. 17 identifies various path lengths including $L_1$ (a distance from a feed location on feed conductor 1703 to the first capacitive coupling location 1705), $L_2$ (a distance from the first capacitive coupling location 1705 to the second capacitive coupling location 1709), $L_3$ (a distance from the feed conductor 1703 to the intermediate conductors 1704 and 1708), $L_4$ (a distance from the intermediate conductors 1704 and 1708 to a plane of the first dipole element 1713 and the second dipole element 1715), $L_5$ (a distance from the plane of the first dipole element 1713 and the second dipole element 1715 to the implanted stimulator 1718), $L_{10}$ (a length of the intermediate conductor 1604 from the capacitive coupling location 1606 to the electrical conductor 1612), and $L_{11}$ (a length of the intermediate conductor 1608 from the capacitive coupling location 1610 to the electrical conductor 1614).

The total path length from a feed location on the feed conductor 1603 to the first dipole element 1613 may be expressed as follows:

$$L_{FirstDipole} = L_1 + L_3 + L_{10} + L_4 \tag{7}$$

The total path length from a feed location on the feed conductor 1603 to the second dipole element 1615 may be expressed as follows:

$$L_{SecondDipole} = L_1 + L_2 + L_3 + L_{11} + L_4 \tag{8}$$

Figure 18B:
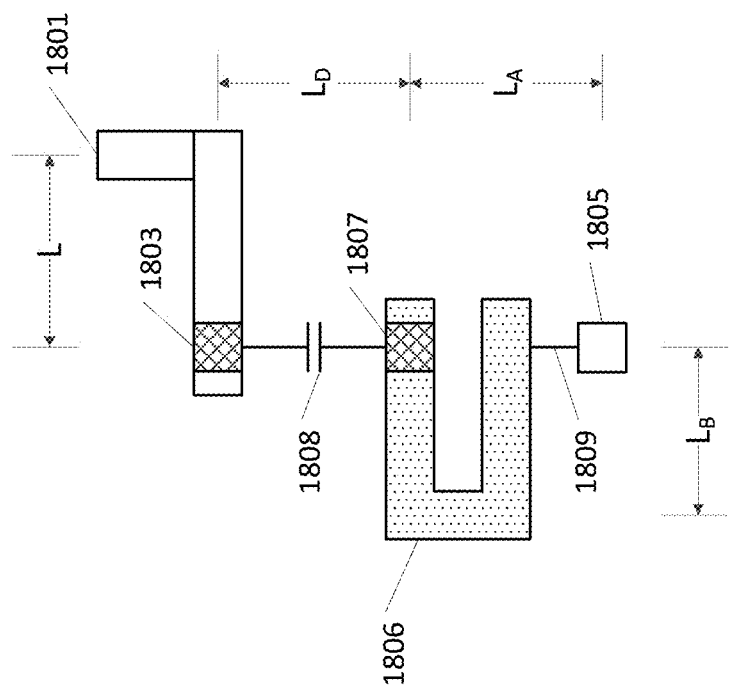
FIG. 18B shows an intermediate conductor capacitively coupled to a feed conductor of a second length, and the intermediate conductor directly coupled to a dipole element.
Figure 18A:
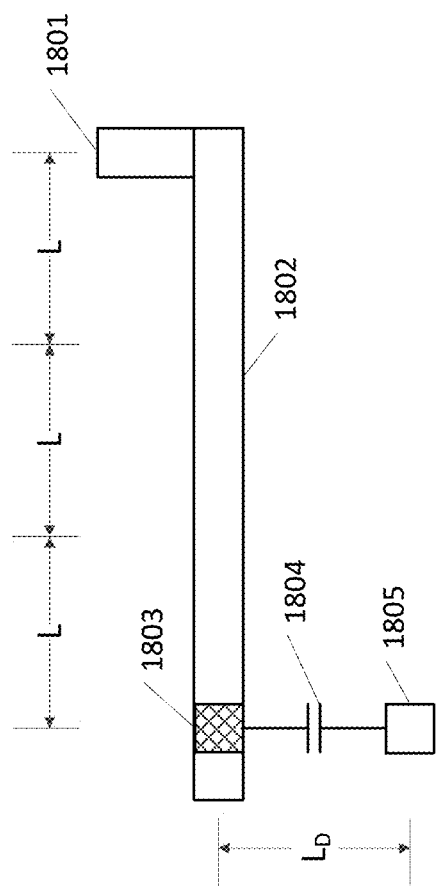
FIG. 18A shows a dipole element capacitively coupled to a feed conductor of a first length.

FIG. 18A shows a dipole element capacitively coupled to a feed conductor of a first length. FIG. 18A shows a radio frequency (RF) feed connector 1801 connected to a feed conductor 1802 at a feed location. The RF feed connector 1801 may comprise one or more electrical conductors that convey an RF signal from a source to the feed connector 1801. The electrical conductors may comprise a coaxial cable, twisted pair(s), or other known RF signal conductors. At location 1803 of the feed conductor 1802, a capacitive coupling 1804 exists with dipole element 1805. The path length from the RF feed connector 1801 to the dipole element 1805 is represented as three lengths L (along feed conductor 1802) and the length $L_D$ (from the feed conductor 1802 to dipole 1805).

FIG. 18B shows an intermediate conductor capacitively coupled to a feed conductor of a second length, and the intermediate conductor directly coupled to a dipole element. FIG. 18B shows an RF feed connector 1801 connected to a feed conductor 1802. At location 1803 of the feed conductor 1802, a capacitive coupling 1807 exists with an intermediate conductor 1806 at a location 1807 of the intermediate conductor 1806. Intermediate conductor curves around and is connected by a conductor 1809 to a dipole element 1805. The path length from the RF feed connector 1801 to the dipole element 1805 is represented as a length L (along feed conductor 1802), the length $L_D$ (from the feed conductor 1802 to the location 1807), a length $L_A$ (a vertical distance from the location 1807 to the dipole element 1805), and two horizontal lengths $L_B$ (from the location 1807 to a distal portion of the intermediate conductor then back to the connection 1809 with the dipole element 1805). A benefit of the configuration of FIG. 18B is the decreased horizontal length of the antenna. This may be achieved, in this FIG. 18B, where the following condition is satisfied:

$$L_A+2L_B>2L \qquad (9)$$

FIG. 19A shows an elevation view of two dipole elements connected to respective conductive layers where the conductive layers have different lengths. FIG. 19A shows an RF feed connector 1901 connected to a feed conductor 1902. At location 1903 of the feed conductor 1902, a capacitive coupling 1904 exists with an intermediate conductor 1906 at a location 1905 of the intermediate conductor 1906. The intermediate conductor 1906 curves around and is connected by a conductor 1911 to a dipole element 1912. The path length from the RF feed connector 1901 to the dipole element 1912 is represented as a combination of a length $L_1$ (along feed conductor 1902), a length $L_D$ (from the feed conductor 1902 to the location 1905), a length $L_5$ (a vertical distance from the location 1905 to the dipole element 1912), and two horizontal lengths $L_3$ (from the location 1905 to a distal portion of the intermediate conductor 1906 then back to the conductor 1911 with the dipole element 1912). Specifically, the path length to the dipole element 1912 may be expressed as follows:

$$L_{1912}=L_1+L_D+L_5+2L_3 \qquad (10)$$

Also, feed conductor 1902 is capacitively coupled 1910 at location 1908 to an intermediate conductor 1907 at location 1909 of the intermediate conductor 1907. An electrical conductor 1913 connects the intermediate conductor 1907 to dipole element 1914. The path length from the RF feed connector 1901 to the dipole element 1914 is represented as a combination of the length $L_1$ (along feed conductor 1902), a length $L_2$ (from location 1903 to location 1908), the length $L_D$ (from the feed conductor 1902 to the location 1909), a length $L_5$ (a vertical distance from the location 1909 to the dipole element 1914), and two horizontal lengths $L_4$ (from the location 1909 to a distal portion of the intermediate conductor 1907 then back to the conductor 1911 with the dipole element 1912). Specifically, the path length to the dipole element 1914 may be expressed as follows:

$$L_{1914}=L_1+L_2+L_D+L_5+2L_4 \qquad (11)$$

FIG. 19B shows an elevation view of two dipole elements connected to respective conductive layers where the conductive layers have different lengths, where the two dipole elements are complementary to those of FIG. 19A. FIG. 19B shows an elevation view of two dipole elements connected to respective conductive layers where the conductive layers have different lengths. FIG. 19B shows an RF feed connector 1915 connected to a feed conductor 1916. At location 1917 of the feed conductor 1916, a capacitive coupling 1918 exists with an intermediate conductor 1919 at a location 1920 of the intermediate conductor 1919. The intermediate conductor 1919 curves around and is connected by a conductor 1921 to a dipole element 1922. The path length from the RF feed connector 1915 to the dipole element 1922 is represented as a combination of a length $L_1$ (along feed conductor 1916), a length $L_D$ (from the feed conductor 1916 to the location 1917), a length $L_5$ (a vertical distance from the location 1917 to the dipole element 1922), and two horizontal lengths $L_3$ (from the location 1920 to a distal portion of the intermediate conductor 1919 then back to the conductor 1921 with the dipole element 1922). Specifically, the path length to the dipole element 1922 may be expressed as follows:

$$L_{1922}=L_1+L_D+L_5+2L_3 \qquad (12)$$

Also, feed conductor 1916 is capacitively coupled 1923 at location 1924 to an intermediate conductor 1925 at location 1926 of the intermediate conductor 1925. An electrical conductor 1927 connects the intermediate conductor 1925 to dipole element 1928. The path length from the RF feed connector 1915 to the dipole element 1928 is represented as a combination of the length $L_1$ (along feed conductor 1916), a length $L_2$ (from location 1917 to location 1924), the length $L_D$ (from the feed conductor 1916 to the location 1926), the length $L_5$ (a vertical distance from the location 1926 to the dipole element 1928), and two horizontal lengths $L_4$ (from the location 1926 to a distal portion of the intermediate conductor 1925 then back to the conductor 1927 with the dipole element 1928). Specifically, the path length to the dipole element 1928 may be expressed as follows:

$$L_{1928}=L_1+L_2+L_D+L_5+2L_4 \qquad (13)$$

The lengths identified in each of FIGS. 4, 6, 15, 16, 17, 18A, 18B, 19A, and 19B are based on planar layouts and rectilinear shapes. It is appreciated that curved shapes may be used as well as the rectilinear shapes are shown for purposes of explanation. For example, if intermediate conductors 1806, 1906, 1907, 1919, and 1925 have curved shapes, the determination of lengths may be based on the actual path lengths of the conductors and not on separate horizontal, vertical, and depth dimensions.

It will be recognized by the skilled person in the art, given the benefit of this disclosure, that the exact arrangement, sizes and positioning of the components in the figures is not necessarily to scale or required. Other embodiments of tissue stimulation systems, tissue stimulators, and methods of manufacturing such tissue stimulators are within the scope of the following claims.

What is claimed is:

1. An antenna comprising:
   two or more feed conductors;
   a plurality of intermediate conductors, each being capacitively coupled to one of the two or more feed conductors;
   a plurality of dipole elements;
   a plurality of electrical conductors, each electrical conductor being connected between at one or more of the intermediate conductors and one or more of the dipole elements; and
   at least one dielectric separating the two or more feed conductors and the plurality of intermediate conductors.

2. The antenna of claim 1, further comprising:
   a plurality of dipole pairs, each dipole pair comprising:
      a first dipole element of the plurality of dipole elements comprising a first proximate end and a first distal end; and
      a second dipole element of the plurality of dipole elements comprising a second proximate end and a second distal end,
   wherein the first proximate end is positioned relative to the second proximate end and separated from the second proximate end by a gap.

3. The antenna of claim 1,
   wherein a first dipole of the plurality of dipole elements comprises a proximate end and a distal end,
   wherein a first intermediate conductor of the plurality of intermediate conductors comprises a proximate end and a distal end,
   wherein an electrical conductor of the plurality of electrical conductors connects a first location of the first dipole and a second location of the first intermediate conductor,
   wherein the first location is spaced from the proximate end of the first dipole, and
   wherein the second location is spaced from the proximate end of the first intermediate conductor.

4. The antenna of claim 1,
   wherein one or more of the plurality of intermediate conductors comprise conductive traces,
   wherein one or more of the plurality of dipole elements comprise conductive traces,
   wherein one or more of the plurality of electrical conductors comprise vias, and
   wherein each via connects one of the plurality of intermediate conductors with one of the plurality of dipole elements.

5. The antenna of claim 1,
   wherein one or more of the plurality of dipole elements comprise conductive wires,
   wherein one or more of the plurality of electrical conductors comprise vias, and
   wherein each via connects one of the plurality of intermediate conductors with one of the plurality of dipole elements.

6. The antenna of claim 1, each of the two or more feed conductors further comprising:
   a feed port,
   wherein the plurality of dipole elements are arranged in dipole pairs, each dipole pair separated by a gap,
   wherein each of the intermediate conductors is connected by one electrical conductor to one of the dipole pairs,
   wherein the gaps are uniform,
   wherein a length of each dipole element is uniform, and
   a length of each intermediate conductor varies by its distance from the feed port.

7. The antenna of claim 6,
   wherein the length of each intermediate conductor increases as distance from the feed port increases.

8. The antenna of claim 6,
   wherein the length of each intermediate conductor decreases as distance from the feed port increases.

9. The antenna of claim 6,
   wherein the gaps form a centerline of the antenna, and
   wherein distal ends of the intermediate conductors, relative to the centerline, are at a common distance from the centerline.

10. The antenna of claim 6,
    wherein the gaps form a centerline of the antenna, and
    wherein proximate ends of the intermediate conductors, relative to the centerline, are at a common distance from the centerline.

11. The antenna of claim 6,
    wherein the gaps form a centerline of the antenna, and
    wherein proximate ends of the intermediate conductors, relative to the centerline, increase in distance from the centerline as distance of the intermediate conductors from the feed port increases.

12. The antenna of claim 6,
    wherein the gaps form a centerline of the antenna, and
    wherein distal ends of the intermediate conductors, relative to the centerline, increase in distance from the centerline as distance of the intermediate conductors from the feed port increases.

13. The antenna of claim 6,
    wherein the gaps form a centerline of the antenna, and
    wherein proximate ends of the intermediate conductors, relative to the centerline, decrease in distance from the centerline as distance of the intermediate conductors from the feed port increases.

14. The antenna of claim 6,
    wherein the gaps form a centerline of the antenna, and
    wherein distal ends of the intermediate conductors, relative to the centerline, decrease in distance from the centerline as distance of the intermediate conductors from the feed port increases.

15. The antenna of claim 1,
    wherein the at least one dielectric comprises a rigid dielectric.

16. The antenna of claim 1,
    wherein the at least one dielectric comprises fabric.

17. An antenna comprising:
    two or more feed conductors, each feed conductor comprising one or more feed ports;
    a plurality of intermediate conductors, each being capacitively coupled to one of the two or more feed conductors;
    a plurality of dipole elements arranged around a centerline;
    a plurality of electrical conductors, each electrical conductor being connected between at one or more of the intermediate conductors and one or more of the dipole elements; and
    at least one dielectric separating the two or more feed conductors and the plurality of intermediate conductors,
    wherein a length of each dipole element is uniform, and
    a length of each intermediate conductor varies by its distance from the feed port.

18. The antenna of claim 17,
wherein the length of each intermediate conductor increases as distance from the feed port increases.

19. The antenna of claim 17,
wherein the length of each intermediate conductor decreases in length as distance from the feed port increases.

20. The antenna of claim 17,
wherein distal ends of the intermediate conductors, relative to the centerline, are at a common distance from the centerline.

21. The antenna of claim 17,
wherein proximate ends of the intermediate conductors, relative to the centerline, are at a common distance from the centerline.

22. The antenna of claim 17,
wherein proximate ends of the intermediate conductors, relative to the centerline, increase in distance from the centerline as distance of the intermediate conductors from the feed port increases.

23. The antenna of claim 17,
wherein distal ends of the intermediate conductors, relative to the centerline, increase in distance from the centerline as distance of the intermediate conductors from the feed port increases.

24. The antenna of claim 17,
wherein the at least one dielectric comprises a rigid dielectric.

25. The antenna of claim 17,
wherein the at least one dielectric comprises fabric.

26. The antenna of claim 17,
wherein proximate ends of the intermediate conductors, relative to the centerline, decrease in distance from the centerline as distance of the intermediate conductors from the feed port increases.

27. The antenna of claim 17,
wherein distal ends of the intermediate conductors, relative to the centerline, decrease in distance from the centerline as distance of the intermediate conductors from the feed port increases.

* * * * *